United States Patent
Harkins et al.

(10) Patent No.: US 11,740,238 B2
(45) Date of Patent: Aug. 29, 2023

(54) COMPOSITIONS AND METHODS OF DETECTING A SUBSTANCE OF INTEREST

(71) Applicant: PIONEER HI-BRED INTERNATIONAL, INC., Johnston, IA (US)

(72) Inventors: Kristi Ruth Harkins, Madrid, IA (US); Aaron Joseph Walck, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 33 days.

(21) Appl. No.: 15/756,807

(22) PCT Filed: Sep. 2, 2016

(86) PCT No.: PCT/US2016/050151
§ 371 (c)(1),
(2) Date: Mar. 1, 2018

(87) PCT Pub. No.: WO2017/040962
PCT Pub. Date: Mar. 9, 2017

(65) Prior Publication Data
US 2018/0252711 A1 Sep. 6, 2018

Related U.S. Application Data

(60) Provisional application No. 62/214,543, filed on Sep. 4, 2015.

(51) Int. Cl.
*G01N 33/569* (2006.01)
*G01N 33/543* (2006.01)

(52) U.S. Cl.
CPC . *G01N 33/56961* (2013.01); *G01N 33/54313* (2013.01)

(58) Field of Classification Search
CPC .................. G01N 33/56961; G01N 33/54313
See application file for complete search history.

(56) References Cited

U.S. PATENT DOCUMENTS

| | | |
|---|---|---|
| 6,406,913 B1 | 6/2002 | Ullman et al. |
| 2003/0232394 A1 | 12/2003 | Kannt et al. |
| 2010/0304403 A1 | 12/2010 | Roby et al. |
| 2012/0149128 A1 | 6/2012 | Manneh |
| 2013/0084652 A1 | 4/2013 | Shapir et al. |
| 2013/0280718 A1 | 10/2013 | Yarnall et al. |

OTHER PUBLICATIONS

Masaki et al. (New Biotechnology, vol. 28, No. 3, Apr. 2011) (Year: 2011).*
Eom et al. ("Quantification analysis of NPT-II protein from genetically modified Vitis vinifera L.," African Journal of Biotechnology vol. 9(23), pp. 3468-3474, published Jun. 7, 2010) (Year: 2010).*

(Continued)

*Primary Examiner* — Shafiqul Haq
*Assistant Examiner* — Nam P Nguyen

(57) ABSTRACT

Disclosed herein are methods and assays for the detection and/or quantification of one or more proteins or substances of interest in a sample, such as a plant, human, insect, microorganism or mammalian sample.

24 Claims, 12 Drawing Sheets

(56) References Cited

OTHER PUBLICATIONS

Eglen et al. ("The Use of AlphaScreen Technology in HTS: Current Status," Current Chemical Genomics, vol. 1, pp. 2-10, published 2008). (Year: 2008).*

Jehan, Tabassum, et al.: "Single nucleotide polymorphism (SNP)—Methods and applications in plant genetics: A review", Indian Journal of Biotechnology, Oct. 2006 (Oct. 2006), vol. 5., pp. 435-459.

Koning: "Light Reactions", Plant Physiology Information Website, 1994, (http://plantphys.info/plant_physiology/lightrxn.shtml).

Peppard, et al.: "Development of a High-Throughput Screening Assay for Inhibitors of Aggrecan Cleavage Using Luminescent Oxygen Channeling (AlphaScreen)" J Biomol Screen, Apr. 2003 (Apr. 2003), vol. 8, No. 2, pp. 149-156.

Perkinelmer, Inc.: "User's Guide to Alpha Assays Protein: Protein Interactions" May 2011 (May 2011), pp. 1-40.

Telfer, Alison, et al.: "Isolated Photosynthetic Reaction Center of Photosystem II as a Sensitizer for the Formation of Singlet Oxygen" The Journal of Biological Chemistry, May 6, 1994 (May 6, 1994), vol. 269, No. 18, pp. 13244-13253.

Zhang, Yi, et al.: "Development of a homogeneous immunoassay based on the AlphaLISA method for the detection of chloramphenicol in milk, honey and eggs" J Sci Food Agric, Jan. 10, 2012 (Jan. 10, 2012), vol. 92, pp. 1944-1947.

The International Search Report and Written Opinion of the International Searching Authority for PCT/US16/50151, dated Nov. 17, 2016.

* cited by examiner

COMPOSITIONS AND METHODS OF DETECTING A SUBSTANCE OF INTEREST

CROSS-REFERENCE TO RELATED APPLICATIONS

This application is a 371 national stage entry of PCT patent application PCT/US16/50151, filed Sep. 2, 2016, which claims priority to U.S. provisional patent application Ser. No. 62/214,543, filed Sep. 4, 2015, herein incorporated by reference in its entirety.

FIELD OF THE INVENTION

The embodiments of the invention relates generally to methods and compositions for the detection and/or quantification of one or more proteins or substances in a sample. Substance-substance interactions, such as protein-protein interactions, may also be determined.

BACKGROUND

Agricultural biotechnology has led to significant improvements in crop productivity worldwide. Development of improved and novel crop varieties requires careful selection and combination of introduced or native traits. Trait performance is often monitored and optimized through detection of key proteins or peptides. High throughput protein screening techniques are often employed for the detection or quantification of proteins or peptides in plant tissues.

SUMMARY OF THE INVENTION

It is an object, feature, and/or advantage to provide herein methods and assays for detecting one or more proteins of interest in a plant sample.

It is another object, feature, and/or advantage to provide herein methods and assays for detecting one or more proteins of interest in a plant sample with reduced background signal.

It is yet another object, feature, and/or advantage to provide herein high throughput methods and assays for detecting one or more proteins of interest that is in a plant sample.

It is still another object, feature, and/or advantage to provide herein sensitive methods and assays for detecting one or more proteins of interest present in low amounts or concentrations in a plant sample.

It is a further object, feature, and/or advantage to provide herein methods and assays for detecting one or more proteins of interest in a plant sample that does not require washing steps.

It is still a further object, feature, and/or advantage to provide herein methods and assays for detecting one or more proteins of interest in a plant sample, where the plant sample does not need to be diluted to reduce photosystem pigment concentration.

It is still a further object, feature, and/or advantage to provide herein methods and assays for detecting one or more proteins of interest in a plant sample, where the background signal is more consistent.

It is an object, feature, and/or advantage to provide herein methods and assays for detecting one or more proteins of interest in a sample using a donor bead that absorbs light at one or more wavelengths.

It is an object, feature, and/or advantage to provide herein methods and assays for detecting one or more substances of interest in a sample using a donor bead that is excited by light at one or more wavelengths.

The present methods and assays for detecting one or more proteins or substances of interest in a sample is not to be limited to or by these objects, features and advantages. No single embodiment need provide each and every object, feature, or advantage.

In one aspect, a method of detecting one or more proteins of interest in a plant sample is provided. The method includes incubating the plant sample having one or more proteins of interest with a donor bead associated with a donor-analyte detection reagent and an acceptor bead associated with an acceptor-associated analyte detection reagent. The donor-associated analyte detection reagent and the acceptor-associated analyte detection reagent are capable of interacting with the one or more proteins of interest. The donor beads can be excited with light having a wavelength outside the range of photosystem absorbance. The emission of light can be captured and the presence or concentration of the protein of interest is determined, for example, from an elevated signal. In another aspect, an assay for detecting one or more proteins of interest in a plant sample includes a plant sample having one or more proteins of interest, an acceptor-associated analyte detection reagent that binds to the one or more proteins of interest, an acceptor bead that associates with the acceptor-associated analyte detection reagent, a donor-associated analyte detection reagent that interacts with the one or more proteins of interest. The donor bead is capable of associating with the donor-associated analyte detection reagent. The donor bead includes a photoactive substance that can be excited by light having a wavelength outside the range of photosystem absorbance.

In another aspect, provided herein is a method of detecting one or more proteins of interest in a plant sample. The method includes incubating the plant sample having one or more proteins of interest with an acceptor bead associated with an acceptor-associated analyte detection reagent, and a peptide or epitope from the protein of interest. The peptide or epitope may be associated with one half of a secondary detection reagent binding pair. A donor bead may be conjugated to or associated with the other half of secondary detection reagent binding pair associated with the epitope or peptide. The donor beads can be excited with light having a wavelength outside the range of photosystem absorbance. The emission of light can be captured and the presence of the protein of interest is determined.

In a still further aspect, an assay of detecting one or more proteins of interest in a plant sample is provided. The assays includes the plant sample having one or more proteins of interest, an acceptor bead conjugated to or associated with an acceptor-associated analyte detection reagent, a peptide or epitope from the protein of interest associated with one half of a secondary detection reagent binding pair, and a donor bead conjugated to or associated with the other half of secondary detection reagent binding pair. The donor bead includes a photoactive substance that can be excited by light having a wavelength outside the range of photosystem absorbance. The emission of light can be captured and the presence of the protein of interest determined.

In another aspect, provided herein is a method of detecting one or more proteins of interest in a plant sample. The method includes incubating the plant sample having one or more proteins of interest with a donor bead associated with a donor-associated analyte detection reagent, and a peptide or epitope from the protein of interest. The peptide or epitope may be associated with one half of a secondary detection reagent binding pair. An acceptor bead may be conjugated to or associated with the other half of secondary detection reagent binding pair associated with the epitope or peptide. The donor beads can be excited with light having a wavelength outside the range of photosystem absorbance. The emission of light can be captured and the presence of the protein of interest determined.

In a still further aspect, an assay of detecting one or more proteins of interest in a plant sample is provided. The assays includes the plant sample having one or more proteins of interest, a donor bead conjugated to or associated with a donor-associated analyte detection reagent, a peptide or epitope from the protein of interest associated with one half of a secondary detection reagent binding pair, and an acceptor bead conjugated to or associated with the other half of secondary detection reagent binding pair. The donor bead includes a photoactive substance that can be excited by light having a wavelength outside the range of photosystem absorbance. The emission of light can be captured and the presence of the protein of interest determined.

In one aspect, provided herein is a method of detecting one or more proteins of interest. The method includes incubating the sample having one or more proteins of interest with a donor bead associated with one or more analyte detection reagents. The analyte detection reagent is capable of interacting with one or more proteins of interest in the sample. The donor beads are capable of absorbing light at more than one wavelength, making it suitable for use with plant, human, insect or mammalian samples. When the donor beads are used with plant samples, the light preferably has a wavelength outside the range of photosystem absorbance. Emission of light is captured. The presence or absence of the one or more proteins of interest of in the sample is determined. The method optionally includes a plant sample having one or more proteins of interest.

In still another aspect, provided herein is a donor bead that is capable of absorbing light at one or more wavelengths. The donor bead may be used in any number of methods and assays.

In yet another aspect, provided herein is a system for detecting one or more proteins of interest. The assay also includes one or more analyte detection reagents that are capable of binding to the one or more proteins of interest. The donor bead associates with the one or more analyte detection reagents. In some embodiments, the donor bead is capable of absorbing light at less than 680 nm and/or above 680 nm or combinations thereof. The assay optionally includes a plant sample having one or more proteins of interest.

In yet another aspect, provided herein is a method of determining interactions between two substances. In one aspect, the method includes incubating a donor bead associated with a substance of interest with an acceptor bead associated with a candidate substance suspected of interacting with the substance of interest. The donor and acceptor beads may be associated with analyte detection reagents and/or secondary detection reagents. The method includes exciting the donor bead with light having a wavelength outside the range of photosystem absorbance, capturing the emission of light and determining whether the substance of interest and candidate substance interact In yet another aspect, an assay of detecting one or more proteins of interest in a plant sample is provided.

In a further aspect, an assay of quantifying one or more proteins of interest in a plant sample is provided.

DESCRIPTION OF THE DRAWINGS

The objects, features, advantages, and technical and industrial significance of the methods and compositions will be better understood by reading the following detailed description of the embodiments, when considered in connection with the accompanying drawings, in which.

DETAILED DESCRIPTION OF THE PREFERRED EMBODIMENTS

Figure 1:
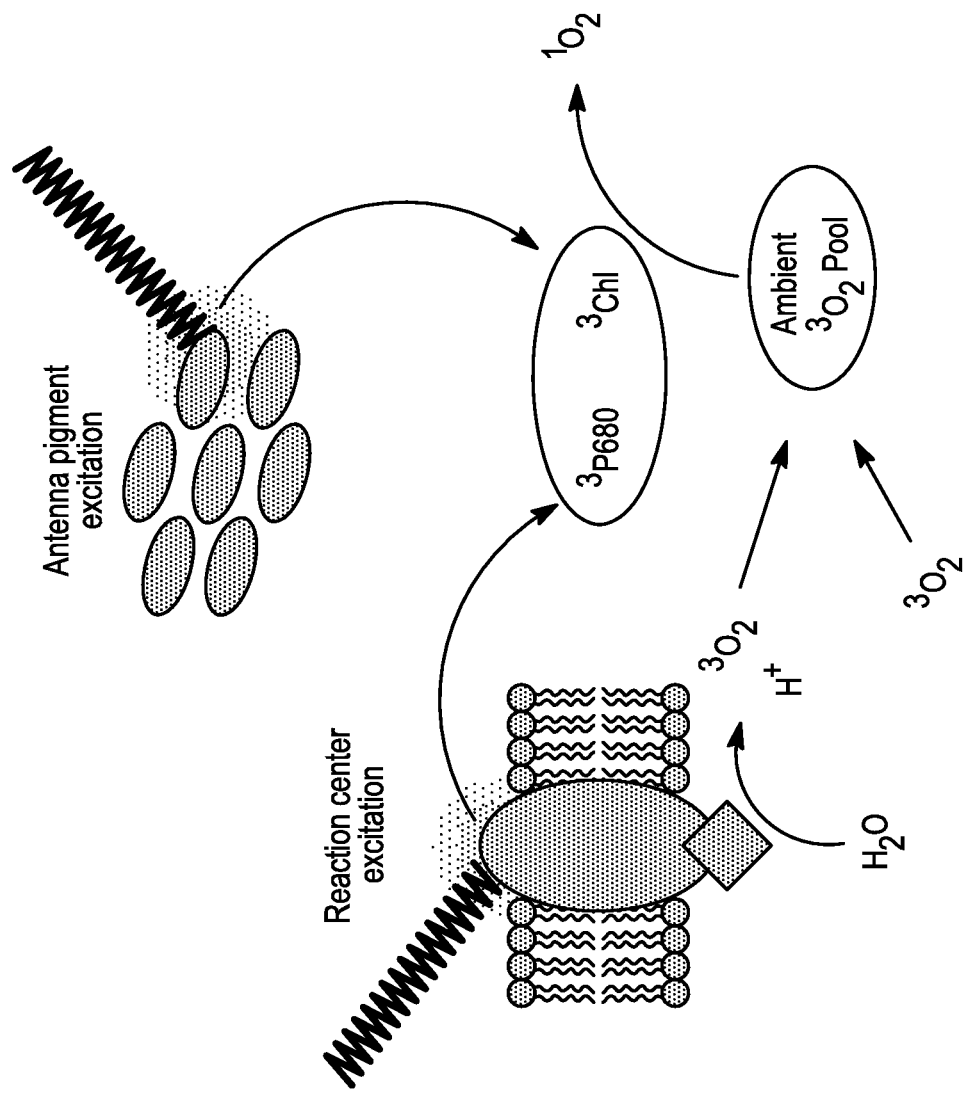
FIG. 1 shows the Singlet Oxygen Production in a Photosynthetic Tissue Extract. Ambient triplet oxygen ($^3O_2$) is present in solution. Triplet oxygen produced from the oxygen evolving complex may contribute to ambient triplet oxygen. Absorbance of light by chlorophyll in antenna pigments and the reaction center leads to production of triplet chlorophyll ($^3$P680, $^3$Chl). Under normal photosynthetic conditions, triplet chlorophyll can be converted back to the unreactive singlet state by nearby quenchers. In the Alpha reaction, quenchers are generally unavailable due to diffusion in the solution. Under assay conditions, a significant portion of triplet chlorophyll reacts with ambient triplet oxygen to produce singlet oxygen.

As used herein, the term "about" applies to all numeric values, whether or not explicitly indicated. The term "about" generally refers to a range of numbers that one would consider equivalent to the recited value (i.e., having the same function or result). In many instances, the term "about" may include numbers that are rounded to the nearest significant figure. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or Figures, should be understood to contemplate the possibilities of including one of the terms, either of the terms, or both terms. For example, the phrase "A or B" will be understood to include the possibilities of "A" or "B" or "A and B."

Various operations may be described as multiple discrete operations in turn, in a manner that may be helpful in understanding embodiments; however, the order of description should not be construed to imply that these operations are order-dependent. Also, embodiments may have fewer operations than described. A description of multiple discrete operations should not be construed to imply that all operations are necessary. Also, embodiments may have fewer operations than described. A description of multiple discrete operations should not be construed to imply that all operations are necessary.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the disclosure.

Disclosed herein in some embodiments are methods and compositions for the detection and/or quantification of one or more proteins of interest or protein-protein interactions in a plant sample. As used herein, the term "protein of interest" refers to any protein, protein variant, functional fragment or derivative thereof that one skilled in the art wishes to detect, quantify or study. As used herein, a "protein variant" is a protein having an amino acid sequence that does not occur in nature. The protein of interest may also be one protein or an interacting set of proteins, such as, without limitation, enzyme/enzyme substrate, receptor/ligand, or antibody/antigen. The protein may be endogenous or heterologous to a plant cell. Endogenous refers to protein that is "native" to, i.e., indigenous to the plant. In contrast, "heterologous" means a protein that originates from a foreign species, or, if from the same species, is substantially modified from its native form in composition and/or genomic locus. The protein of interest may be a fusion or recombinant protein. "Fusion" refers to a protein that includes two or more nucleic acid sequences that originally coded for separate proteins. "Recombinant" refers to an artificial combination of two otherwise separated segments of sequence.

The protein of interest includes without limitation a protein that confers a trait for agronomics, insect resistance, disease resistance, herbicide resistance, sterility, grain characteristics, oil, starch, carbohydrate, phytate, protein, nutrient, metabolism, digestibility, kernel size, sucrose loading, and commercial products. Accordingly, exemplary proteins of interest include without limitation, *Bacillus thuringiensis* toxic protein CRY34, CRY35, CRY1F, CRY1AB, VIP3A, CRY2A.127, CRY1A.88, detoxification proteins fumonosin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); proteins that confer resistance to herbicides such as acetolactate synthase (ALS), sulfonylurea-type herbicides such as chlorosulfuron (e.g., the S4 and/or Hra mutations in ALS); glutamine synthase, such as phosphinothricin or basta (e.g., the bar gene); glyphosate (e.g., the EPSPS gene or the GAT gene; see for example patent publications US20040082770 and WO 03/092360), alpha amylase, see for example U.S. Pat. No. 8,013,218, selectable and/or screenable marker proteins including phosphinothricin acetyl transferase (PAT), e.g. monocot or maize optimized PAT, phosphomannose isomerase (PMI) U.S. Pat. No. 5,767,378, kinases, heat shock proteins, transcription factors, and the like.

The protein of interest may be the only protein present in the sample or the protein of interest may be present with other proteins of interest or other proteins, such as in a complex protein sample.

"Plant" includes reference to whole plants, plant organs, plant tissues, leaves, seeds and plant cells and progeny of same. Plant cells include, without limitation, cells from seeds, suspension cultures, embryos, meristematic regions, callus tissue, roots, shoots, gametophytes, sporophytes, pollen, microspores and photosynthetic tissue such as leaves. As used herein, a "plant sample" refers to a plant material that has or is suspected of having one or more proteins of interest. In particular examples of the methods and compositions disclosed herein, the plant sample is a tissue from a plant, including but not limited to alfalfa tissue, *Arabidopsis* tissue, bean tissue, canola tissue, cassava tissue, corn tissue, rice tissue, rye tissue, sorghum tissue, soybean tissue, sugarcane tissue, triticale tissue, and/or wheat tissue. In some examples, the plant tissue is photosynthetic tissue, including but not limited to, from the leaf of a plant, including but not limited to alfalfa leaf tissue, *Arabidopsis* leaf tissue, bean leaf tissue, canola leaf tissue, cassava leaf tissue, corn leaf tissue, rice leaf tissue, rye leaf tissue, sorghum leaf tissue, soybean leaf tissue, sugarcane leaf tissue, triticale leaf tissue, and/or wheat leaf tissue.

In particular examples of the methods and compositions disclosed herein, the plant sample is an extract from a plant, for example, the tissue of a plant. The extract may be from a photosynthetic tissue. In some embodiments, the plant tissue extract is tissue-specific, for example, including without limitation, from a leaf or stem or combination thereof. In particular examples of the methods and compositions disclosed herein, the plant sample is a protein extract from a plant. For example, the protein extract may be obtained from a photosynthetic tissue of a plant. In some examples, the protein extract is from leaf tissue, stem tissue or a combination thereof. The tissue or protein extract may be obtained from any plant, including without limitation, alfalfa photosynthetic tissue, *Arabidopsis* photosynthetic tissue, bean photosynthetic tissue, canola photosynthetic tissue, cassava photosynthetic tissue, corn photosynthetic tissue, rice photosynthetic tissue, rye photosynthetic tissue, sorghum photosynthetic tissue, soybean photosynthetic tissue, sugarcane photosynthetic tissue, triticale photosynthetic tissue, and/or wheat photosynthetic tissue.

In some embodiments, the plant sample is from a plant that has undergone genome editing, for example, using a double-strand-break-inducing agent, such as but not limited to a Zinc Finger endonuclease, a meganuclease, a TALEN endonuclease, a CRISPR-Cas guideRNA or other polynucleotide guided double strand break reagent, and the plant has or is suspected of having one or more proteins of interest. In some embodiments, the plant sample is from a transgenic plant. The plant sample may be from a transgenic plant that has or is suspected of having one or more proteins of interest. "Transgenic" refers to any cell, tissue, plant part or plant, the genome of which has been altered by the presence of a heterologous nucleic acid, such as a recombinant DNA construct, including those initial transgenic events as well as those created by sexual crosses or asexual propagation from the initial transgenic event. "Transgenic plant" includes reference to a plant which comprises within its genome a heterologous polynucleotide. The heterologous polynucleotide may be integrated into the genome alone or as part of a recombinant DNA construct.

Examples of suitable plants include but are not limited to alfalfa, apple, apricot, *Arabidopsis*, artichoke, arugula, asparagus, avocado, banana, barley, beans, beet, blackberry, blueberry, broccoli, brussel sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, *eucalyptus*, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, *papaya*, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugar beet, sugarcane, sunflower, sweet potato, sweet gum, tangerine, tea, tobacco, tomato, triticale, turf, turnip, a vine, watermelon, wheat, yams, and zucchini.

In some embodiments, the plant sample is a protein sample. The protein sample may be prepared or obtained, for example, from a commercial source, such as P-PER Plant Protein Extraction Reagent (ThermoFisher Cat#89803); ReadyPrep Protein Extraction Kit (BioRad Cat#163-2086). In some examples, the protein sample is a protein extract. Protein extracts may be obtained by a variety of techniques. Examples of such techniques include, but are not limited to, mechanical or chemicals means or a combination thereof. Protein extraction may be accomplished by fragmenting plant tissue and solubilizing the fragmented tissue in an extraction buffer. In other examples, protein can be extracted from tissue that is frozen, lyophilized or from freshly collected tissue. The tissue may be whole or fragmented. Fragmentation may be accomplished using any suitable technique, for example, by grinding by mortar and pestle, Geno/Grinder, and the like. The tissue may be fragmented in the presence or absence of extraction buffer. Samples may be processed individually or in groups, for example, by containers. The containers may be vials, plates, such as a 96-well megatiter plate.

In some embodiments, the method of detecting a protein of interest in a plant sample includes incubating the plant sample having or suspect of having the protein of interest with an analyte detection reagent associated with an acceptor bead and an analyte detection reagent associated with a donor bead. As used herein, "analyte detection reagent" can be or include any substance that binds to, or interacts chemically with, a protein of interest or another detection reagent.

Exemplary analyte detection reagents for use in the methods and compositions disclosed herein include without limitation ligands such as antibodies, enzymes, aptamers, or other agents having specific affinity to the protein of interest. The acceptor-associated detection reagent and the donor-associated analyte detection reagent may be the same or different type of reagent.

In some examples, the donor and acceptor beads used in the methods and compositions described herein may have the same type of analyte detection reagent, for example, the donor and acceptor beads may both use antibodies as analyte detection reagents (e.g., sandwich assay format for detection of protein(s) of interest). In some embodiments, the antibodies on the donor and acceptor beads have specific affinity to distinct epitopes of the same protein of interest. The distinct epitopes may be overlapping or non-overlapping.

Alternatively, a competitive assay format for detecting a protein of interest in a plant sample is also provided. The acceptor-associated analyte detection reagent is a competitive reagent that is capable of binding to or interacting with the protein of interest. This competitive assay format may include a competitive agent, including without limitation, an antibody, a peptide or epitope from the protein of interest, or other molecule, such that the antibody, a peptide, epitope or molecule can bind to the acceptor-associated analyte detection reagent. In some embodiments, the method and assay includes incubating acceptor beads conjugated or preconjugated to an acceptor-associated analyte detection reagent, the plant sample having a protein of interest, a peptide or epitope from the protein of interest associated with one half of a secondary detection reagent binding pair, and a donor bead conjugated to or associated with the other half of the secondary detection reagent binding pair. In the absence of the protein of interest in the plant sample, the donor and acceptor beads come together around the competitive reagent to generate light upon excitation of the donor bead. When the protein of interest is present in the plant sample, the emission of light will decrease as compared to the control that does not contain the protein of interest.

In yet, another embodiment, a competitive assay format for detecting a protein of interest in a plant sample, a competitive agent, which has similar affinity characteristics when compared to the protein of interest, is associated with the acceptor bead. This competitive agent may include without limitation, an antibody, a peptide or epitope from the protein of interest, or other molecule, such that the antibody, peptide, epitope or molecule can bind to the donor-associated analyte detection reagent. In some embodiments, the method and assay includes incubating donor beads which are associated with, conjugated to, or preconjugated to a donor-associated analyte detection reagent, the plant sample having a protein of interest, and a peptide or epitope from the protein of interest which is associated with, conjugated to, or preconjugated to an acceptor bead. In the absence of the protein of interest in the plant sample, the donor and acceptor beads come together around the competitive reagent to generate light upon excitation of the donor bead. When the protein of interest is present in the plant sample, the emission of light will decrease as compared to the control that does not contain the protein of interest.

The acceptor-associated detection reagent and the donor-associated analyte detection reagent are able to associate with the acceptor and donor beads respectively.

As used herein, the term "associated with" refers to a covalent or non-covalent bond between the acceptor or donor bead and the analyte detection reagent. The acceptor or donor bead may be associated with the analyte detection reagent using any suitable technique or composition. For example, a protocol to conjugate antibodies to donor and/or acceptor beads is known. See PerkinElmer® AlphaLISA® Assay Development Guide at world wide web at perkinelmer.com/Content/manuals/GDE_AlphaLisaDevelopment-Guide.

For example, the donor and/or acceptor bead and the analyte detection reagent may be associated using a linker, a functional group, or a coating. See, for example, U.S. Pat. Nos. 5,340,716; 5,516,636; 5,536,834; 5,709,994; 5,763,602; 6,251,581; 6,406,667; 6,797,481; 7,033,775; 7,101,682; N. J. Turro, "Molecular Photochemistry", page 132, W. A. Benjamin Inc., New York 1965; Ullman, et al., Proc. Natl. Acad. Sci. USA 91, 5426-5430 (1994); Strong et al, Ann. New York Acad. Sci., 745: 297-320 (1994); Martin et al, Methods Enzymol., 186: 635-645 (1990); Yarmush et al, Crit. Rev. Therapeutic Drug Carrier Syst., 10: 197-252 (1993); Wohrle, Chimia, 45: 307-310 (1991); Thetford, European patent publ. 0484027; Sessler et al, SPIE, 1426: 318-329 (1991); Madison et al, Brain Research, 522: 90-98 (1990); Polo et al, Inorganica Chimica Acta, 192: 1-3 (1992); and Demas et al, J. Macromol. Sci., A25: 1189-1214 (1988). In some embodiments, association is achieved using streptavidin/avidin and biotinylation. For example, the acceptor bead may be coated with streptavidin or avidin and the acceptor-analyte detection reagent biotinylated, e.g. a biotinylated anti-protein of interest antibody.

The acceptor-associated detection reagent may be associated with the acceptor bead prior to or during incubation with the protein of interest. The donor-associated analyte detection reagent may be associated with the donor bead prior to or during incubation with the protein of interest. In some examples, the analyte detection reagent and the acceptor bead are preconjugated. In some embodiments, the analyte detection reagent is an antibody that is directly conjugated to the acceptor and/or donor bead. In some examples, the donor and/or acceptor beads may be preconjugated to the analyte detection reagent, such as tags described elsewhere herein and known to one skilled in the art. The incubation may occur for a time sufficient for the complex, e.g. protein of interest-analyte detection reagent-acceptor bead, to form. Accordingly, one embodiment of detecting one or more proteins of interest includes incubating the plant sample having one or more proteins of interest with an analyte detection reagent. The detection agent is capable of directly or indirectly binding to the protein of interest and the acceptor bead to form a complex comprising the protein of interest, the binding agent and the acceptor bead. As mentioned herein, in some embodiments, this may be accomplished by directly conjugating or coating the analyte detection reagent to the bead.

In yet other embodiments, donor beads may be preconjugated, conjugated or coated with the analyte detection reagent. Examples include without limitation, streptavidin/avidin coated donor beads that bind to biotinylated antibodies, glutathione coated donor beads that bind to GST-tagged proteins, nickel chelate coated donor beads that bind to His-tagged proteins, Protein A coated donor beads that bind to antibodies and Fc-fusion proteins, donor beads conjugated to antibodies such as anti-rabbit IgG antibodies, anti-mouse IgG antibodies, anti-FLAG antibodies, anti-DIG antibodies or combinations thereof.

In yet other embodiments, acceptor beads may be pre-conjugated, conjugated or coated with the analyte detection reagent. Examples include without limitation, acceptor beads conjugated to an anti-His antibody that can capture His-tagged proteins, acceptor beads conjugated to an anti-bovine IgG antibody that can capture bovine IgG antibodies, anti-bovine IgG2 antibody that can capture bovine IgG2 antibodies, acceptor beads conjugated to anti-chicken IgY antibody that can capture chicken IgY antibodies, acceptor beads conjugated to mouse monoclonal anti-digoxin antibody that can capture Dig-labeled proteins, anti-FLAG antibodies, anti-goat IgG antibodies, anti-hemagglutinin (HA) antibody, anti-MBP (maltose-binding protein) antibody that can be used to capture MBP-tagged proteins, anti-mouse IgM antibodies, anti-rabbit IgG antibodies, anti-sheep IgG antibodies, acceptor beads, glutathione coated beads that bind to GST-tagged proteins, nickel chelate coated beads that bind to His-tagged proteins, acceptor beads conjugated to Protein G, acceptor beads coated with anti-bovine IgA antibodies to capture bovine IgA antibodies, acceptor beads conjugated with anti-bovine IgG1 antibodies to capture bovine IgG1 antibodies, acceptor beads conjugated with anti-bovine IgM antibodies to capture bovine IgM antibodies, acceptor beads conjugated to anti-c-myc antibody to capture c-myc-tagged proteins, acceptor beads conjugated to anti-FITC antibody that can capture FITC-tagged and fluorescein-labeled biomolecules, acceptor beads coated with anti-GFP antibody that recognize wildtype and recombinant GFP (rGFP), and cross-reacts with eGFP, acceptor beads conjugated to anti-GST antibodies that can capture GST-tagged proteins, acceptor beads conjugated to anti-mouse IgA antibodies that can capture mouse IgA antibodies, acceptor beads conjugated to anti-V5 antibody that can detect proteins tagged with the V5 14-amino-acid tag, acceptor beads conjugated to Protein A that can capture antibodies that capture antibodies that associate with Protein A, acceptor beads conjugated to Protein L that can capture antibodies that bind Protein L, acceptor beads conjugated to streptavidin that can be used to capture biotinylated proteins, and the like and combinations thereof.

Figure 11:
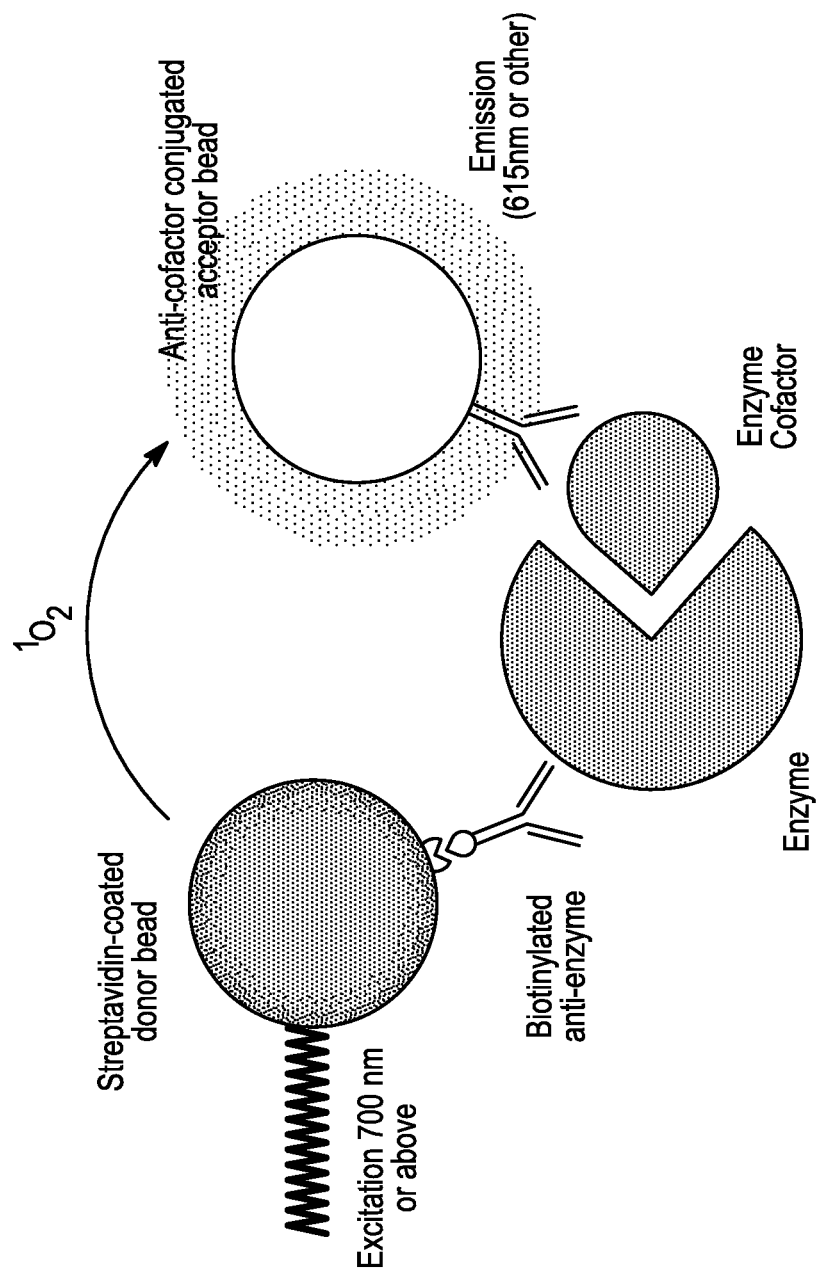
FIG. 11 is a cartoon showing one example of an assay for determining protein-protein interactions in a plant sample that reduces background signal. The donor bead is excited by light having a wavelength outside the range of photosystem absorbance.

In other embodiments, the beads and analyte detection reagent may be preconjugated, conjugated to or coated with secondary reagents. Examples of secondary reagents include but are not limited to ligands, receptors, antibodies, antigens, lipids, carbohydrates, peptides, oligosaccharides, lectins, nucleic acids, aptamers, epitope tags such as a polyhistidine tag, a metal bound by a polyhistidine tag, biotin, avidin, streptavidin, and digoxigenin. Examples of binding pairs include, without limitation, enzyme/enzyme substrate; receptor/ligand, antibody/antigen; polyhistidine tag/metal; nucleic acid/substantially complementary nucleic acid, nucleic acid/complementary nucleic acid, avidin/biotin or streptavidin/biotin. See, for example, one embodiment provided in FIG. 11.

The order of addition of the components may be varied. In some examples, the acceptor beads, donor beads, and analyte detection reagents, whether or not associated with beads, and sample, e.g. a plant sample, may be added simultaneously. Alternatively, the acceptor beads, donor beads, and analyte detection reagents, whether or not associated with beads, and sample, e.g. a plant sample, can be combined wholly or partially sequentially. One or more incubation steps may be involved after some or all of the components are combined, i.e. acceptor beads, donor beads, analyte detection reagents, whether or not associated with beads, and sample, e.g. a plant sample. The incubation generally ranges from about 30 seconds to 6 hours, more usually from about 2 minutes to 1 hour.

In some cases, the incubation time may be for a period of time sufficient for the acceptor and donor beads to come into proximity prior to signal detection. In some examples, the incubation time is from 10 seconds to 5 min or for a longer periods of time, for example 5-10 min, 10-20 min, 20-40 min, 40-60 min, 1-2 hours or longer, e.g. overnight. The incubating may be performed in different temperature conditions depending on different embodiments, e.g. the type of the protein of interest to be detected or type of an analyte detection agent, donor and/or acceptor beads used for the detection, etc.

The incubation step is carried out under conditions suitable for biomolecular interaction and activity. The assay mixture generally includes an aqueous medium. The pH of the assay mixture is usually in the range of about pH 2.5 to about pH 9. One or more buffers can be included in the assay mixture illustratively including, but not limited to, borate, cacodylate, carbonate, citrate, HEPES, MES, MOPS, phosphate, PIPES, TAPS, TES and Tris buffers. Temperatures employed in assays of the present invention are generally in the range of about 4° C. to about 37° C., preferably at room temperature.

The sample, e.g. plant sample, with the protein or substance of interest, acceptor beads, donor beads, analyte detection reagents and optionally secondary detection reagents may be added using any suitable instruments and techniques, for example, using a manual pipette, a liquid handler, or robotic or automated equipment.

As described herein, the term "bead" refers to a solid-phase support particle. The bead may be organic or inorganic. The bead may be porous or non-porous and substantially non-soluble in an aqueous medium. The bead may be solid, semi-solid, gel or a mixture thereof. The bead may be in the form of a plate, a chip, a fiber, a mesh, a pin, a membrane, such as a nitrocellulose membrane; a container; and a cell or cell membrane. The bead may be coated, for example, with a hydrogel to minimize non-specific binding and self-aggregation. The beads may be of any suitable size that can be used for the methods and compositions disclosed herein. The beads can be micromolar in diameter, for example, 1 μm, 2 μm, 3 μm, 4 μm, 5 μm, 6 μm, 7 μm, 8 μm, 9 μm, and 10 μm, or nanomolar in diameter, for example, 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, or 300 nm. The bead, acceptor or donor bead, may be composed of any material so long as it is capable of associating with the analyte detection reagent or secondary analyte detection reagent. Exemplary bead materials include without limitation latex, glass, metal, ceramic, plastic, such as polycarbonate, polypropylene, polystyrene, nylon, paper, silicon, cellulose, nitrocellulose, agarose, dextran, polyacrylamide and the like or combinations thereof.

Figure 2:
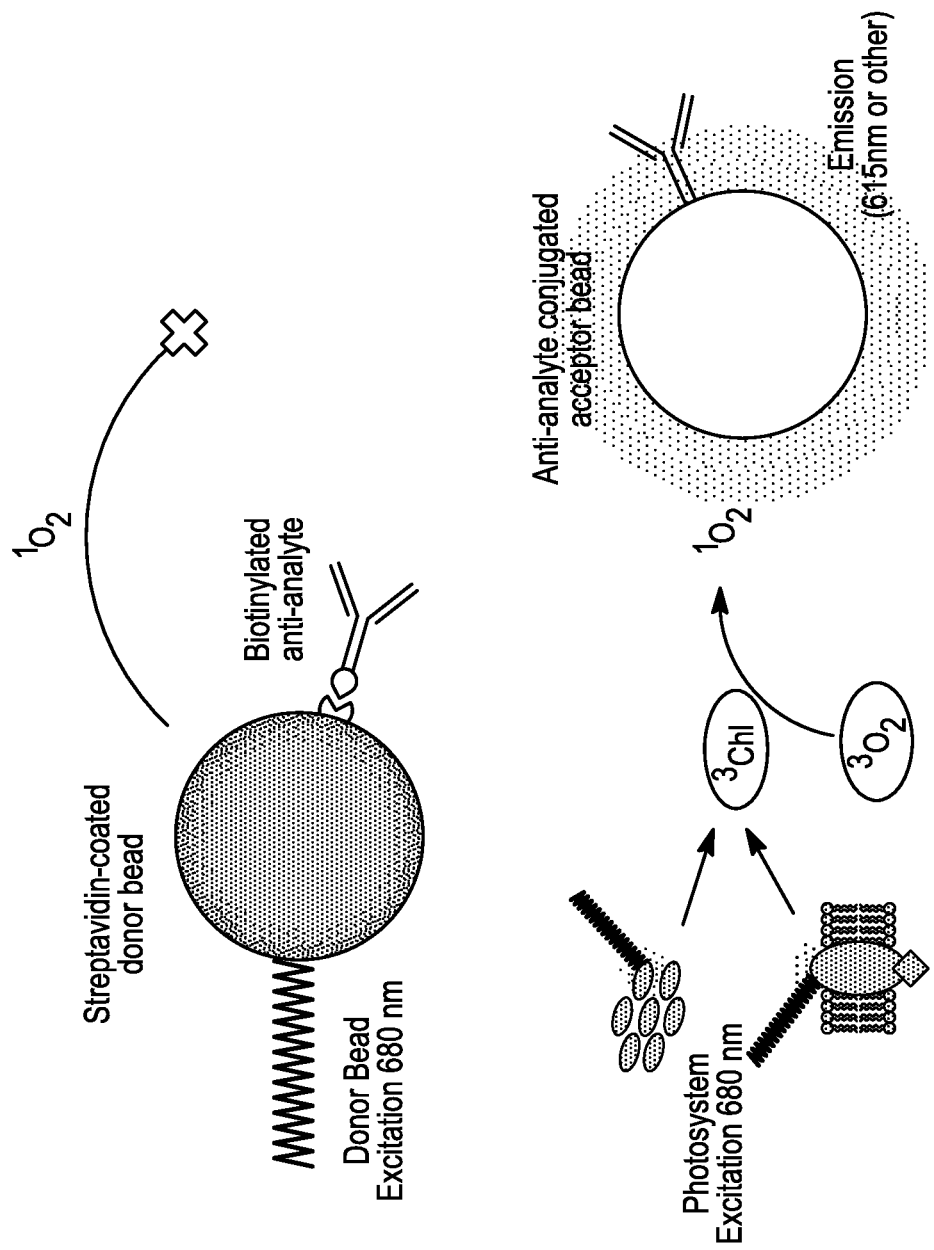
FIG. 2 shows the Mechanism of Background Signal Production by Photosynthetic Tissue. When using traditional Alpha donor beads (commercially available PerkinElmer), the reaction well must be illuminated with intense light at 680 nm. Along with the excitement of donor beads, this leads to the production of triplet chlorophyll which reacts with ambient oxygen to form singlet oxygen. In the absence of protein of interest, singlet oxygen produced during donor excitation does not reach the acceptor bead because the two beads are not held in close proximity. When photosynthetic tissue matrix is present in a negative Alpha reaction well, singlet oxygen formed from nearby photosystem components causes emission of the acceptor bead and quantitation of false signal.

In one embodiment, the methods and compositions disclosed herein include exciting the donor bead with light having a wavelength outside the range of photosystem absorbance for a particular plant. This range may vary with plant species and tissue type. For example, if the protein of interest being detected is from a maize leaf sample, the donor bead would be excited with a wavelength that is outside the range of photosystem absorbance for a maize leaf. For example, if the protein of interest being detected is from a soy leaf sample, the donor bead would be excited with a wavelength that is outside the range of photosystem absorbance for a soy leaf. As used herein, a wavelength outside the range of photosystem absorbance refers to a wavelength of light that (1) when used to excite a donor bead reduces, minimizes and/or ablates the amount of singlet oxygen formed from nearby photosystem components, such as photosystem pigments, of a plant sample, for example, as outlined in FIG. 1, thereby reducing, minimizing and/or ablating photosystem-derived emission from the acceptor bead that receives and is excited by the singlet oxygen, for example, as outlined in FIG. 2, and/or (2) is not absorbed or has low absorbance by photosystem pigments. The reduction, minimization, and/or ablation of photosystem-derived emission from the acceptor bead and/or absorbance by photosystem pigments of the plant sample may be determined in comparison to a control. One skilled in the art would be able to ascertain whether the wavelength was outside of the range of photosystem absorbance, for example, by conducting experiments, such as those disclosed herein in Example 5. As used herein, photosystem includes pigments found in plants, such as but not limited to chlorophyll a, chlorophyll b, pheophytin, carotenoids, such as but not limited to beta-carotene and zeaxanthin, xanthophylls such as but not limited to lutein, anthocyanins, betalains and the like. In one example, the donor bead is excited with light having a wavelength that chlorophyll a, chlorophyll b, pheophytin, carotenoid and/or xanthophyll does not absorb.

The donor bead may include a photoactive substance that alone or in combination with other compounds can be photoactivated by absorption of light having wavelengths about 200 nm to about 670 nm or about 690 nm to about 1100 nm. In some embodiments, the donor beads are excited with a wavelength below about 400 nm. In other embodiments, the donor beads are excited with a wavelength within, from or about 550 nm to about 650 nm, or within, from or about 700 nm or above.

The donor beads may be made of or include one or more materials that reacts with or is excitable by light preferably at wavelengths below 680 nm or above 680 nanometers (nm). The material, when excited is capable of transferring or emitting singlet oxygen molecules to an acceptor bead. The acceptor beads, after receiving the singlet oxygen molecules, emit light. In some embodiments, the acceptor bead is made of or includes one or more materials that utilize singlet oxygen to emit light. The light may be fluorescent, phosphorescent or chemiluminescent light. The luminescence, either chemiluminescence or fluorescence, produced upon reaction of the photoactive substance with singlet oxygen can be at any suitable wavelength. In some examples, the emission wavelength is below the wavelength of the excitation wavelength to minimize autofluorescence.

Without wishing to be bound by any particular theory or mechanism, it is believed that excitation of the donor bead with one or more wavelengths of light that minimizes or limits photosystem absorbance by plant photosystem pigment will reduce or minimize background signal from a plant sample. In some examples, use of photoactive substances in the donor bead that absorb light at wavelengths below or above 680 nm will reduce background signal by reducing the light emitted from the absorbance and activation of a plant's photosystem, for example, maize and/or soy, which is excited by a wavelength of 680 nm, for example, chlorophyll. Background chemiluminescence signal may be reduced by 5%, 10%, 15%, 20%, 25%, 30%, 35%, 40%, 45%, 50%, 55%, 60%, 65%, 70%, 75%, 80%, 85%, 90%, 95%, or 100% as compared to a control, wherein the donor bead is excited with light having a wavelength outside the range of photosystem absorbance for the plant sample, for example, a wavelength less than 680 nm or greater than 680 nm. A "control" refers to a sample or standard used for comparison with an experimental sample. In some examples, a control refers to donor beads that are subjected to light at a wavelength where photosystem pigments in the plant sample also absorb light and become excited, e.g. subjected to light at a wavelength within the range of photosystem absorbance for the plant sample, but are otherwise subjected to the same treatment as donor beads that are excited with light having a wavelength outside the range of photosystem absorbance for the plant sample. In some embodiments, the control is a historical control or standard reference value or range of values, such as a previously tested control sample, such as a group of samples that represent baseline or normal values.

Background chemiluminescence signal may be reduced by 5%, 10%, 15%, 20%, 25%, 30%, 35%, 40%, 45%, 50%, 55%, 60%, 65%, 70%, 75%, 80%, 85%, 90%, 95%, or 100% as compared to a control, wherein emission is captured at a wavelength that is lower than the wavelength of excitation of the donor bead.

Use of the methods and compositions disclosed herein may increase the sensitivity of the detection and/or quantification of the protein of interest by 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some examples, a control refers to donor beads that are excited by light at a wavelength where photosystem pigments in the plant sample also absorb light and become excited, e.g. subjected to light at a wavelength within the range of photosystem absorbance for the plant sample, but are otherwise subjected to the same treatment as donor beads that are excited with light having a wavelength outside the range of photosystem absorbance for the plant sample. In some embodiments, the control is a historical control or standard reference value or range of values, such as a previously tested control sample, such as a group of samples that represent baseline or normal values.

Use of the methods and compositions disclosed herein may decrease the variability of the background signal by 5%, 10%, 15%, 20%, 25%, 30%, 35%, 40%, 45%, 50%, 55%, 60%, 65%, 70%, 75%, 80%, 85%, 90%, 95%, or 100% as compared to a control. In one example, a control refers to donor beads that are excited by light at a wavelength where photosystem pigments in the plant sample also absorb light and become excited, e.g. subjected to light at a wavelength within the range of photosystem absorbance for the plant sample, but are otherwise subjected to the same treatment as donor beads that are excited with light having a wavelength outside the range of photosystem absorbance for the plant sample. In some embodiments, the control is a historical control or standard reference value or range of values, such as a previously tested control sample, such as a group of samples that represent baseline or normal values.

Exemplary photoactive substances for inclusion in the donor beads include but are not limited to, carbocyanine, such as 1,1',3,3,3',3'Hexamethylindotricarbocyanine iodide, 1,1'-Diethyl-2,2'-dicarbocyanine iodide, 1,1'-Diethyl-4,4'-dicarbocyanine iodide, 3,3'-Diethylthiatricarbocyanine iodide, 3,3'-Diethylthiatricarbocyanine perchlorate; Naphthalocyanine, such as 2,11,20,29-Tetra-tert-butyl-2,3-naphthalocyanine, 2,3-Naphthalocyanine, 5,9,14,18,23,27,32,36-

Octabutoxy-2,3-naphthalocyanine, Cobalt(II) 2,3-naphthalocyanine, Copper(II) 5,9,14,18,23,27,32,36-octabutoxy-2,3-naphthalocyanine, Nickel(II) 5,9,14,18,23,27,32,36-octabutoxy-2,3-naphthalocyanine, Silicon 2,3-naphthalocyanine bis(trihexylsilyloxide), Silicon 2,3-naphthalocyanine dichloride, Silicon 2,3-naphthalocyanine dihydroxide, Silicon 2,3-naphthalocyanine dioctyloxide, Tin (IV) 2,3-naphthalocyanine dichloride, Vanadyl 2,11,20,29-tetra-tert-butyl-2,3-naphthalocyanine, Vanadyl 2,3-naphthalocyanine, Zinc 2,11,20,29-tetra-tert-butyl-2,3-naphthalocyanine; Phthalocyanine, such as 1,4,8,11,15,18,22,25-Octabutoxy-29H,31H-phthalocyanine, 2,3,9,10,16,17,23,24-Octakis(octyloxy)-29H,31H-phthalocyanine, 2,9,16,23-Tetra-tert-butyl-29H,31H-phthalocyanine, 29H,31H-Phthalocyanine β-form, Aluminum 1,8,15,22-tetrakis(phenylthio)-29H,31H-phthalocyanine chloride, Aluminum 2,9,16,23-tetraphenoxy-29H,31H-phthalocyanine chloride, Aluminum phthalocyanine hydroxide, Cobalt(II) phthalocyanine β-form, Copper(II) 1,2,3,4,8,9,10,11,15,16,17,18,22,23,24,25-hexadecafluoro-29H,31H-phthalocyanine, Copper(II) 1,4,8,11,15,18,22,25-octabutoxy-29H,31H-phthalocyanine, Disodium phthalocyanine, Gallium(III)-phthalocyanine chloride, Indium(III) phthalocyanine chloride, Lead(II) phthalocyanine, Lead(II) tetrakis(4-cumylphenoxy)phthalocyanine, Manganese(II) phthalocyanine, Manganese(III) phthalocyanine chloride, Nickel(II) 1,4,8,11,15,18,22,25-octabutoxy-29H,31H-phthalocyanine, Poly(copper phthalocyanine), Silicon phthalocyanine dichloride, Titanium(IV) phthalocyanine dichloride, Titanyl phthalocyanine, Titanyl phthalocyanine γ-modification, Vanadyl 2,9,16,23-tetraphenoxy-29H,31H-phthalocyanine, Vanadyl 3,10,17,24-tetra-tert-butyl-1,8,15,22-tetrakis(dimethylamino)-29H,31H-phthalocyanine, Zinc 1,4,8,11,15,18,22,25-octabutoxy-29H,31H-phthalocyanine, and Zinc phthalocyanine; unspecified conjugated/ring dyes or pigments, such as IR-1048, IR-1050, IR-1051, IR-1061, IR-140, IR-775 chloride, IR-780 iodide, IR-783, IR-792, IR-797 chloride, IR-806, IR-813 perchlorate, IR-820, IR-895 and Naphthol Green B Technical grade or combinations thereof. In some examples, the photoactive substances are dyes or pigments. Suitable pigments and dyes are mentioned herein and also include without limitation, for example, chemiluminescent dyes, infrared dyes, phthalocyanine, and porphyrin dyes, and other photonic and optical materials, see, for example, known photonic and optical materials disclosed by Sigma Aldrich (St. Louis Mo.). In some examples, the photoactive substance, including the dye or pigment may be modified, for example, a hydrogen replaced with a hydroxide group, etc. Modified and/or non-modified photoactive substances or combinations thereof, including but not limited to modified and/or non-modified dyes or pigments or combinations thereof, may be used or incorporated in the donor beads so long as the donor bead comprises one or more materials that reacts with or is excitable by light at the desired wavelength. Suitable methods and techniques for making beads, such as donor beads, are described, for example, in U.S. Pat. Nos. 5,340,716, and 8,486,719, and US Published Patent Application No. 20110124001.

TABLE 1

Examples of dyes and/or pigments (with chemical name) and approximate absorption wavelengths that may be employed in the donor beads in the compositions and methods described herein.

| Chemical name | Type | Approximate Absorption Wavelength |
| --- | --- | --- |
| Copper(II) 1,2,3,4,8,9,10,11,15,16,17,18,22,23,24,25-hexadecafluoro-29H,31H-phthalocyanine | Phthalocyanine | 689 nm |
| Titanium(IV) phthalocyanine dichloride | Phthalocyanine | 692 nm |
| Titanyl phthalocyanine | Phthalocyanine | 692 nm |
| Titanyl phthalocyanine γ-modification | Phthalocyanine | 692 nm |
| Gallium(III)-phthalocyanine chloride | Phthalocyanine | 694 nm |
| 2,9,16,23-Tetra-tert-butyl-29H,31H-phthalocyanine | Phthalocyanine | 695 nm |
| Indium(III) phthalocyanine chloride | Phthalocyanine | 697 nm |
| 29H,31H-Phthalocyanine β-form | Phthalocyanine | 698 nm |
| Aluminum phthalocyanine hydroxide | Phthalocyanine | 698 nm |
| Lead(II) phthalocyanine | Phthalocyanine | 698 nm |
| 2,3,9,10,16,17,23,24-Octakis(octyloxy)-29H,31H-phthalocyanine | Phthalocyanine | 701 nm |
| Aluminum 2,9,16,23-tetraphenoxy-29H,31H-phthalocyanine chloride | Phthalocyanine | 701 nm |
| Zinc phthalocyanine | Phthalocyanine | 701 nm |
| Silicon phthalocyanine dichloride | Phthalocyanine | 702 nm |
| 1,1'-Diethyl-2,2'-dicarbocyanine iodide | Carbocyanine | 707 nm |
| Vanadyl 2,9,16,23-tetraphenoxy-29H,31H-phthalocyanine | Phthalocyanine | 710 nm |
| 2,3-Naphthalocyanine | Naphthalocyanine | 712 nm |
| Lead(II) tetrakis(4-cumylphenoxy)phthalocyanine | Phthalocyanine | 713 nm |
| Naphthol Green B Technical grade | Unspecified conjugated/ring | 714 nm |
| Disodium phthalocyanine | Phthalocyanine | 721 nm |
| Manganese(III) phthalocyanine chloride | Phthalocyanine | 726 nm |
| Manganese(II) phthalocyanine | Phthalocyanine | 727 nm |

TABLE 1-continued

Examples of dyes and/or pigments (with chemical name) and approximate absorption wavelengths that may be employed in the donor beads in the compositions and methods described herein.

| Chemical name | Type | Approximate Absorption Wavelength |
| --- | --- | --- |
| Silicon 2,3-naphthalocyanine bis(trihexylsilyloxide) | Naphthalocyanine | 729 nm; 774 nm |
| Cobalt(II) 2,3-naphthalocyanine | Naphthalocyanine | 731 nm |
| Zinc 1,4,8,11,15,18,22,25-octabutoxy-29H,31H-phthalocyanine | Phthalocyanine | 736 nm |
| 1,1',3,3,3',3'-Hexamethylindotricarbocyanine iodide | Carbocyanine | 740 nm |
| Copper(II) 1,4,8,11,15,18,22,25-octabutoxy-29H,31H-phthalocyanine | Phthalocyanine | 740 nm |
| Nickel(II) 1,4,8,11,15,18,22,25-octabutoxy-29H,31H-phthalocyanine | Phthalocyanine | 743 nm |
| Aluminum 1,8,15,22-tetrakis(phenylthio)-29H,31H-phthalocyanine chloride | Phthalocyanine | 759 nm |
| 3,3'-Diethylthiatricarbocyanine perchlorate | Carbocyanine | 760 nm |
| 1,4,8,11,15,18,22,25-Octabutoxy-29H,31H-phthalocyanine | Phthalocyanine | 762 nm |
| 3,3'-Diethylthiatricarbocyanine iodide | Carbocyanine | 765 nm |
| Zinc 2,11,20,29-tetra-tert-butyl-2,3-naphthalocyanine | Naphthalocyanine | 769 nm |
| IR-775 chloride | Unspecified conjugated/ring | 775 nm |
| IR-780 iodide | Unspecified conjugated/ring | 780 nm |
| Silicon 2,3-naphthalocyanine dichloride | Naphthalocyanine | 780 nm |
| IR-783 | Unspecified conjugated/ring | 782 nm |
| 2,11,20,29-Tetra-tert-butyl-2,3-naphthalocyanine | Naphthalocyanine | 784 nm |
| Silicon 2,3-naphthalocyanine dihydroxide | Naphthalocyanine | 785 nm |
| IR-792 | Unspecified conjugated/ring | 792 nm |
| IR-797 chloride | Unspecified conjugated/ring | 797 nm |
| Silicon 2,3-naphthalocyanine dioctyloxide | Naphthalocyanine | 798 nm |
| IR-806 | Unspecified conjugated/ring | 806 nm |
| Vanadyl 2,11,20,29-tetra-tert-butyl-2,3-naphthalocyanine | Naphthalocyanine | 808 nm |
| Vanadyl 3,10,17,24-tetra-tert-butyl-1,8,15,22-tetrakis(dimethylamino)-29H,31H-phthalocyanine | Phthalocyanine | 810 nm |
| IR-813 perchlorate | Unspecified conjugated/ring | 813 nm |
| 1,1'-Diethyl-4,4'-dicarbocyanine iodide | Carbocyanine | 814 nm |
| Vanadyl 2,3-naphthalocyanine | Naphthalocyanine | 817 nm |
| IR-820 | Unspecified conjugated/ring | 820 nm |
| IR-140 | Unspecified conjugated/ring | 823 nm |
| Nickel(II) 5,9,14,18,23,27,32,36-octabutoxy-2,3-naphthalocyanine | Naphthalocyanine | 848 nm |
| Copper(II) 5,9,14,18,23,27,32,36-octabutoxy-2,3-naphthalocyanine | Naphthalocyanine | 853 nm |
| 5,9,14,18,23,27,32,36-Octabutoxy-2,3-naphthalocyanine | Naphthalocyanine | 867 nm |
| Tin(IV) 2,3-naphthalocyanine dichloride | Naphthalocyanine | 875 nm |
| IR-895 | Unspecified conjugated/ring | 895 nm |
| IR-1048 | Unspecified conjugated/ring | 1048 nm |
| IR-1050 | Unspecified conjugated/ring | 1048 nm |
| IR-1051 | Unspecified conjugated/ring | 1051 nm |
| IR-1061 | Unspecified conjugated/ring | 1061 nm |
| Cobalt(II) phthalocyanine β-form | Phthalocyanine | Unspecified |
| Poly(copper phthalocyanine) | Phthalocyanine | Unspecified |

In one embodiment, the donor bead comprises carbocyanine, naphthalocyanine, phthalocyanine, a dye, or a pigment with an unspecified conjugated/ring structure or combinations thereof.

In some embodiments, the donor bead contains or includes one or more materials, such as pigments and/or dyes, that are excited by light at a wavelength from 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1010 nm, 1020 nm, 1030 nm, 1040 nm, 1050 nm, 1060 nm, 1070 nm, 1080 nm, 1090 nm, or 1100 nm or combinations thereof. Upon excitation, the donor bead produces singlet oxygen.

In some embodiments, the donor bead contains or includes one or more materials, such as pigments and/or dyes, that are excited by light at a wavelength from at least or about 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1010 nm, 1020 nm, 1030 nm, 1040 nm, 1050 nm, 1060 nm, 1070 nm, 1080 nm, 1090 nm, or 1100 nm or combinations thereof and less than or about 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1010 nm, 1020 nm, 1030 nm, 1040 nm, 1050 nm, 1060 nm, 1070 nm, 1080 nm, 1090 nm, or 1100 nm or combinations thereof. Upon excitation, the donor bead produces singlet oxygen.

The one or more acceptor beads include one or more materials, that alone or in combination, is excitable by singlet oxygen so that the bead releases energy or emits light. The light may be fluorescent, phosphorescent or chemiluminescent light. The luminescence, either chemiluminescence or fluorescence, is produced upon reaction of the material with singlet oxygen. In some embodiments, the acceptor beads emit light with a wavelength of about 615 nm.

Additional materials excitable by singlet oxygen to release energy include without limitation include chemiluminescence reactants. Chemiluminescence reactants are capable of reacting with singlet oxygen such that energy is transferred to a material comprised in the acceptor bead when it is in proximity to the donor bead. Exemplary chemiluminescence reactants include, but are not limited to, thioxenes, such as 1,4-thioxenes. See, for example, Ullman et al., PNAS, USA, 91:5426-5439, 1994, and U.S. Pat. Nos. 5,340,716; 5,516,636; 5,536,834; 5,709,994; 5,763,602; 6,251,581; 6,406,667; 6,797,481; 7,033,775; and 7,101,682 for additional examples of these and other materials that are excitable by singlet oxygen and methods of making these materials.

Additional materials excitable by singlet oxygen to release energy that may be included in acceptor beads include without limitation non-limiting examples of such fluorescent dyes generally include polycyclic aromatic hydrocarbon fluorescent dyes such as anthracene dyes illustratively including 9,10-bis(phenylethynyl)anthracene (BPEA), 9,10-diphenylanthracene (DPA), 9,10-dibromoanthracene, and derivatives thereof such as halogen and/or alkyl substituted anthracenes illustratively including 1-chloro-9,10-bis(phenylethynyl)anthracene, 2-chloro-9,10-bis(phenylethynyl)anthracene, 2-ethyl-9,10-bis(phenylethynyl)anthracene and 1,2-dimethyl-9,10-bis(phenylethyl)anthracene; napthacene dyes illustratively including tetraphenylnaphthacene (rubrene) and 5,12-bis(phenylethynyl)napthacene, coumarins, oxazine dyes; phthalocyanines, porphyrins; polyacetylenes, squaraines, and such dyes as 4-acetamido-4'-isothiocyanatostilbene-2,2'-disulfonic acid; acridine and derivatives such as acridine and acridine isothiocyanate; 4-amino-N-[3-vinylsulfonyl)phenyl]naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarins and derivatives such as coumarin, 7-amino-4-methylcoumarin (AMC, Coumarin 120), 7-amino-4-trifluoromethylcouluarin (Coumaran 151); cyanosine; DAPDXYL sulfonyl chloride; 4',6-diaminidino-2-phenylindole (DAPI); 5',5"-dibromopyrogallol-sulfonephthalein (Bromopyrogallol Red); 7-diethylamine-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylaminolnaphthalene-1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-aminoethyl)amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), 5-(4,6-dichlorotriazin-2-yl)aminofluorescein (DTAF), 2', 7'-dimethoxy-4', 5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino]ethyl}amino)naphthalene-1-sulfonic acid), Malachite Green isothiocyanate; 4-methyl umbelliferone; orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron™ Brilliant Red 3B-A); rhodamine and derivatives such as 6-carboxy-X-rhodamine (ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N',N-tetramethyl-carboxyrhodamine (TAMRA); tetramethyl rhodamine; tetramethyl rhodamine isothiocyanate (TRITC); riboflavin; rosolic acid; bis-(4-dimethlyaminophenyl)squaraine; lanthanide chelates and cryptates such as, but not limited to, chelates and cryptates of dysprosium, erbium, europium, praseodymium, samarium, terbium, thulium, and ytterbium; chrysene; coronene; naphthalene; phenanthrene; pyrene; and perylene or combinations thereof. Additional acceptor materials are described in Lakowicz, J. R., Principles of Fluorescence Spectroscopy, Springer, 3rd ed., 2006; and Haughland, R. P., The Handbook, A Guide to Fluorescent Probes and Labeling Technologies, 10th Ed., 2005. Additional materials excitable by singlet oxygen to release energy that may be included in acceptor beads include without limitation non-limiting examples of 9-thioxanthone, acetone, metalloporphyrins, such as hematoporphyrin, fullerenes, benzophenone, methylene blue, rose Bengal and derivatives and combinations thereof.

In one embodiment, the acceptor bead comprises thioxene, anthracene, rubrene, europium, terbium, or samarium or combinations thereof. Acceptor beads may be made or purchased. Suitable methods and techniques for making acceptor beads are described, for example, in U.S. Pat. Nos. 8,486,719 and 5,340,716, and U.S. Published Patent Application No. 20110124001. Acceptor beads are commercially available, for example, from PerkinElmer, including AlphaScreen® (thioxene, anthracene, rubrene containing acceptor beads), AlphaLISA® (europium containing acceptor beads), and Alphaplex™ (terbium, samarium or other containing acceptor beads).

In some examples, the methods and compositions disclosed herein include one or more donor beads that have one or more different excitation wavelengths. These donor beads may be used in methods, assays and compositions for plant, insect, microorganism, human or animal samples.

In some examples, the donor bead is excited by light at a wavelength from 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1010 nm, 1020 nm, 1030 nm, 1040 nm, 1050 nm, 1060 nm, 1070 nm, 1080 nm, 1090 nm, or 1100 nm or combinations thereof. In some examples, light having two or more wavelengths may be used to excite the donor bead, for example, including a wavelength that is within the range of photosystem absorbance of the plant sample and a wavelength that is outside the range of photosystem absorbance of the plant sample, so long as the light used to excite the donor beads reduces, minimizes and/or ablates the amount of singlet oxygen formed from nearby photosystem components of the plant sample and/or is not absorbed or has low absorbance by photosystem pigments of the plant sample. For illustration purposes, donor beads may be excited with light having wavelengths of about 680 nm and about 780 nm and be considered suitable for use with the methods described herein so long as the light used to excite the donor beads reduces, minimizes, and/or ablates the amount of singlet oxygen formed from nearby photosystem components of the plant sample and/or is not absorbed or has low absorbance by photosystem pigments of the plant sample and/or reduces chemiluminescence background signal in comparison to using light of a wavelength within the range of photosystem absorbance of the plant sample. In some embodiments, excitation of the donor bead may be by any suitable wavelength of light that minimizes or limits photosystem absorbance by plant photosystem pigments.

In some examples, the donor beads are excited by a wavelength from at least about 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, or 670 nm and less than about 680 nm, 670 nm, or 660 nm.

The donor beads are excited at least by a wavelength from at least about 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1010 nm, 1020 nm, 1030 nm, 1040 nm, 1050 nm, 1060 nm, 1070 nm, 1080 nm, 1090 nm, or 1100 nm and less than about 1100 nm.

In some cases, the donor bead is excited at about 700 nm. In other examples, the donor bead is excited at about 780 nm. Upon excitation, the donor bead produces singlet oxygen, which leads to emission from nearby acceptor beads.

The light may be a relatively narrow band of wavelengths corresponding to the target excitation wavelength of the donor bead, e.g. above the range of photosystem absorbance for a particular plant if the sample is a plant sample. Without wishing to be bound by this theory, excitation could be achieved by excitation with a wide range of wavelengths, which may optionally be filtered through a bandpass filter to limit the range of wavelengths. Light for excitation can be produced, for example, by a laser, such as a diode laser, a flash lamp, or other light source. An optical apparatus may be used to focus excitation light within the donor-acceptor-analyte detection reagent-protein complex. The excitation may occur for a period sufficient for the donor beads to become activated, e.g. release singlet oxygen, and then stopped, gradually or abruptly. Prior to detection of the emission signal, if desired, a delay of controlled interval may be observed to allow for the dissipation of background signal.

In some examples, the methods and compositions disclosed herein include one or more types of acceptor beads that have different emission wavelengths. The emission of light may be captured at a wavelength from 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1010 nm, 1020 nm, 1030 nm, 1040 nm, 1050 nm, 1060 nm, 1070 nm, 1080 nm, 1090 nm, or 1100 nm or combinations thereof. In one embodiment, the emission is captured at a wavelength that is lower than the wavelength of excitation. For example, the donor bead is excited by light at a wavelength of about 700n or about 780 nm (or from about 700 nm to 785 nm) and emission of light may be captured at a wavelength of 615 nm (or from about 610 nm to 620 nm).

The luminescence or light produced by the excited acceptor beads of the present compositions and methods can be detected and/or quantified using any suitable technique or instrument. For example, light may be detected and/or quantified by any appropriately configured fluorescence or chemiluminescence reader such as a fluorimeter or any other convenient means to determine the amount of protein present in the plant sample. Means for detection include, but are not limited to, a spectrometer, a fluorimeter, a photometer, a detection device commonly incorporated with a chromatography instrument such as, but not limited to, a size exclusion-high performance liquid chromatography, such as, but not limited to, an EnSpire® Multimode, EnVision® Multi-label Plate Readers, BMG Pherastar fluorimeter, or Biotek Synergy.

For cases of multiplexed reaction, multiple emission wavelengths may be combined in a single emission signal. To capture two emission wavelengths simultaneously, emission signal can be passed any device that that is capable of selectively splitting or filtering light based on wavelength to split the signal. Unlimited examples include but are not limited to a dichroic mirror, a longpass dichroic mirror, a beamsplitter, an optical filter or combinations thereof and the like that are capable of selectively splitting or filtering light based on wavelength. Long-pass dichroic mirrors work by allowing passage of light above a specified wavelength while reflecting below a specified wavelength. Light from both signals can be conditioned using an emission filter, then photons from each signal can be counted on separate photomultipliers.

Accordingly described herein are methods and compositions detecting or determining the presence/absence of one or more proteins of interest in a sample, e.g. a plant sample. In some examples, 1, 2, 3, 4, 5, 6, 7, 8, 9, 10 or more proteins of interest may be detected or quantified in a sample, e.g. a plant sample. The detection or quantification can be determined using a sensor configured to convey the presence or absence of a protein of interest as either a "positive" or a "negative" result. In some embodiments, the protein of interest is quantified to determine the concentration of the protein of interest in the sample. A quantitative signal may be proportional to the concentration of the protein of interest (e.g., a noncompetitive assay) or inversely proportional to the concentration of the protein of interest (e.g., a competitive assay).

When the level of protein of interest detected or quantified is present in the sample in low amounts, the assays, methods, and systems optionally include optimizing protein expression of the protein of interest, increasing the protein of interest in a different sample by increasing the copy number of coding sequence that encodes the protein of interest, modifying the coding sequence that encodes the protein of interest, such as codon-optimization, or modifying the promoter or regulatory elements that are driving the coding sequence encoding the protein of interest until the desired level of protein is detected in the sample. In addition to or alternatively, when the level of protein of interest detected or quantified is present in the sample in low amounts, decisions are made on protein presence, absence, or range specific expression; and the assays, methods, and systems optionally include culling plants that express the protein of interest in improper amounts, or growing or breeding plants which express the protein of interest in proper amounts.

The following specific examples are given but are not meant to limit the scope of the claims in any way.

EXAMPLES

Example 1. Observation of Photosynthetic Background Signal from Leaf Tissue Extract Methods To determine the effect of photosynthetic tissue extract on AlphaLISA™ chemistry (PerkinElmer, Waltham, Mass.), negative leaf extract was loaded into an AlphaLISA® assay (PerkinElmer, Waltham, Mass.) in the presence of various protein of interest concentrations. PBST extraction buffer was prepared by addition of 0.05% Tween-20 detergent to a 1× reconstitution of Chloride-Phosphate Mixture (Cat# PW0002-30, EMD Millipore, Billerica Mass.). A serial dilution of purified protein of interest was prepared using PBST extraction buffer as diluent. Within the serial dilution, analyte concentration ranged from 10-0.2 pg/µl, as well as a buffer sample which did not contain protein of interest.

5/16" punches were collected from known negative corn leaf tissue. Leaf punches were extracted in 1.2 ml titertubes (Cat#84501XNBZQ, Quality Scientific Plastics, San Diego Calif.). For extraction, 2 leaf punches were added to the tube, along with 700 µl PBST extraction buffer and two 3/16" ball bearings (Daisy Outdoor Products, Rogers Ark.). Samples were macerated using a Geno/Grinder (SPEX SamplePrep, Metuchen N.J.), then centrifuged for 10 minutes at 3889×G and 4° C. to pellet debris. Leaf extract was removed from the tubes and pooled before preparing serial dilutions using PBST extraction buffer as diluent. Dilution factors within the extract serial dilution series were: undiluted, 2.5, 5, 10, 25 and 50.

Each point of the analyte serial dilution series was diluted at a 1:1 ratio using PBST extraction buffer and each of the extract serial dilution points to yield an array of serial dilution sets, each containing an array of protein of interest concentrations in either PBST or extract dilutions. Each analyte/extract serial dilution series contained analyte ranging from 5 to 0.1 pg/µl, as well as a solution that did not contain protein of interest. Each analyte/extract serial dilution series contained a differing concentration of sample extract. Final concentrations were 1:2 extract, 1:5 extract, 1:10 extract, 1:20 extract, 1:50 extract, 1:100 extract, and PBST extraction buffer only.

AlphaLISA® reagents, including biotinylated antibody, antibody-conjugated AlphaLISA acceptor beads and donor beads, were diluted to previously optimized concentrations using 1× AlphaLISA® assay buffer (Cat # AL000, PerkinElmer, Waltham Mass.) as diluent. To prepare AlphaLISA reaction plates, 5 µl of each analyte/extract serial dilution series was added in triplicate to the wells of a white half-area 96-well plate (Cat#6005560, PerkinElmer, Waltham Mass.). 10 µl of each biotinylated antibody solution and acceptor bead solution were added to all assay wells. 25 µl donor bead solution was added to all assay wells. Reaction plates were incubated for 1 hour at room temperature, protected from light. Following incubation, reaction plates were read using an EnVision Turbo (PerkinElmer, Waltham, Mass.). Data was analyzed using Microsoft Excel.

Results and Conclusions

Figure 3:
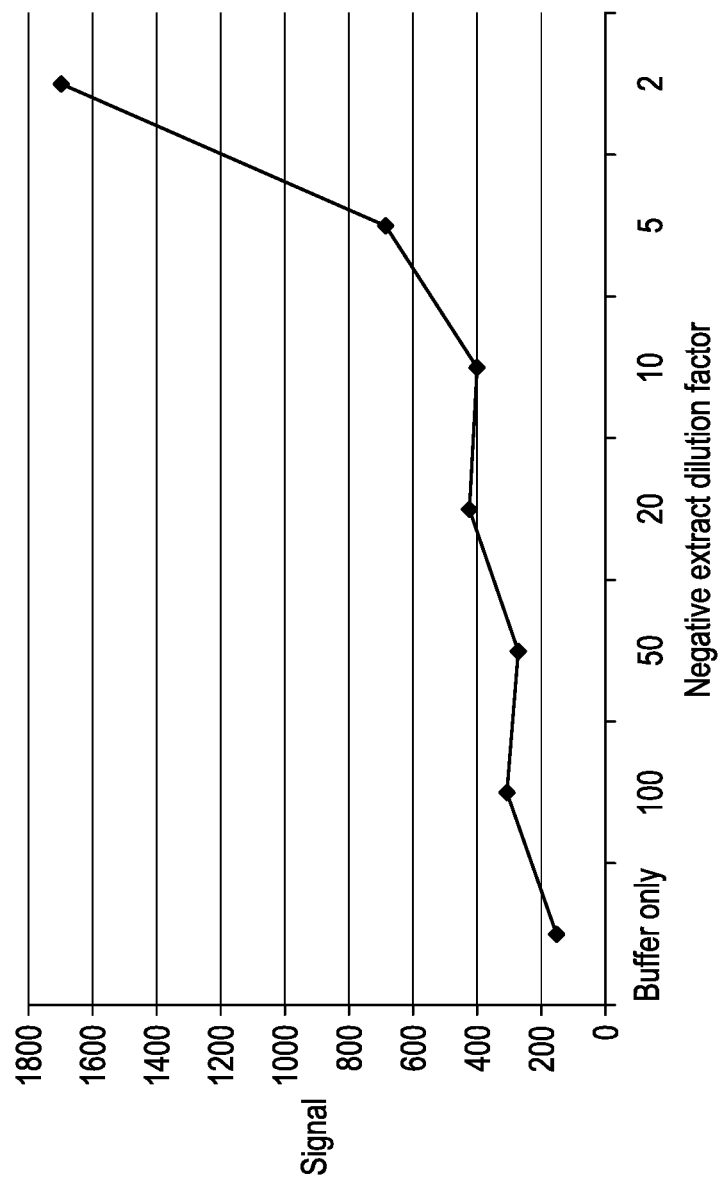
FIG. 3 shows background signal for wells which contained negative leaf extract and lacked protein of interest. X-axis represents leaf extract titer (buffer only and 1:100 to 1:2 dilutions). Y-axis represents signal. Background signal generally increases with increasing negative extract titer.
Figure 4:
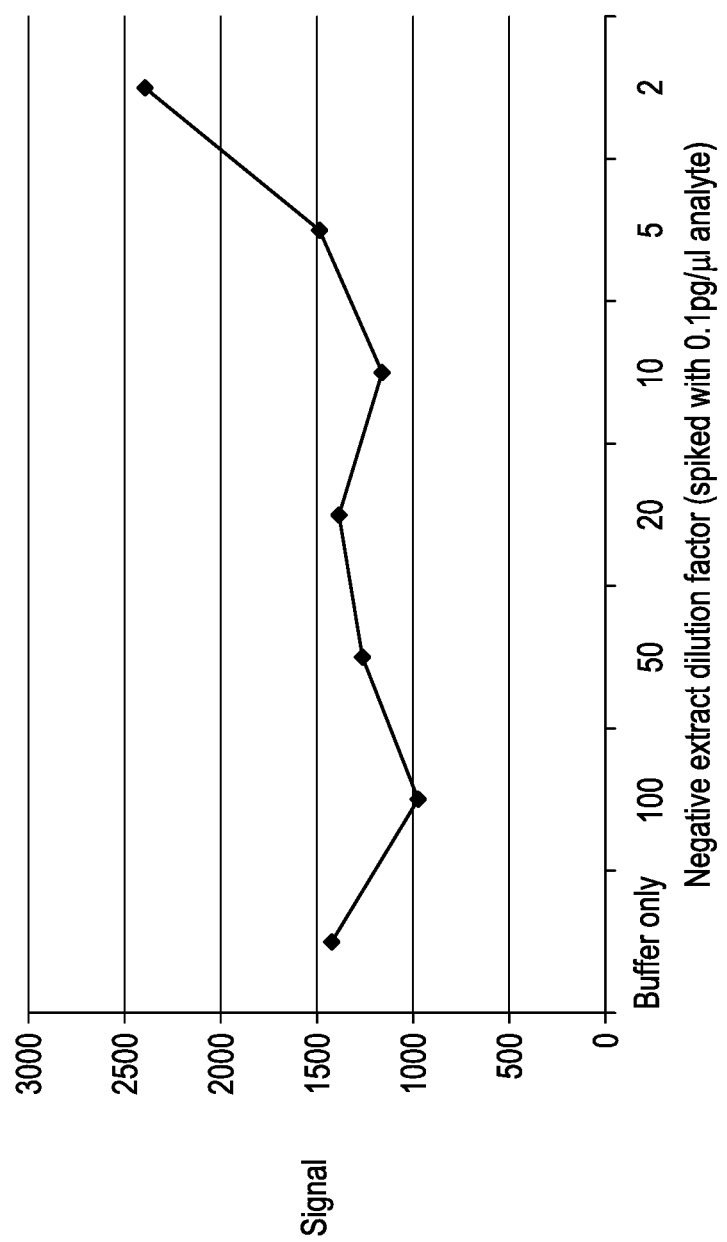
FIG. 4 shows background signal for wells which contained negative leaf extract and 0.1 pg/μl target analyte. X-axis represents leaf extract titer (buffer only and 1:100 to 1:2 dilutions). Y-axis represents signal. Background signal is highest for highest negative extract titer (1:2).

Background signal was observed in wells which contained negative tissue extract but lacked protein of interest. For wells containing negative extract, but lacking analyte, magnitude of background signal increased with increasing tissue extract titer (FIG. 3). This trend was also observed in wells containing low concentrations of analyte (FIG. 4). Correlation between background signal and negative extract titer suggests negative extract causes background signal.

Example 2: AlphaLISA Component Evaluation Using Negative Extract

To investigate how negative extract influenced AlphaLISA™ chemistry, leaf tissue was run in the presence of components of the AlphaLISA® assay. Negative tissue was collected and extracted as described in Example 1 above. Following extraction of negative tissue, a serial dilution series was prepared using PBST as diluent. Final extract dilution factors were: undiluted extract, 1:2 extract and 1:10 extract. For separate AlphaLISA® assays targeting different analytes, biotinylated antibody, antibody-conjugated acceptor, and donor beads were diluted to previously optimized concentrations using 1× AlphaLISA® assay buffer as diluent.

AlphaLISA® assays were prepared by adding 10 µl extract to the wells of a reaction plate. Total reaction volume of 100 µl was used. For each of the two assay chemistries used, wells were prepared using the following schematics:
a) 10 µl extract+90 µl AlphaLISA® assay buffer
b) 10 µl extract+20 µl antibody-conjugated acceptor solution+70 µl AlphaLISA® assay buffer
c) 10 µl extract+20 µl of each biotinylated antibody and antibody-conjugated acceptor solutions+50 µl AlphaLISA® assay buffer
d) 10 µl extract+20 µl of each biotinylated antibody and antibody-conjugated acceptor solutions+50 µl donor bead solution Following reaction preparation, plates were incubated at room temperature protected from light. 10 µl of reaction mixture was transferred to a 384-well proxiplate (Cat#6006290, PerkinElmer, Waltham Mass.) after 40 minutes of incubation, 95 minutes of incubation and 120 minutes of incubation. Proxiplates were read using Envision detector (PerkinElmer, Waltham, Mass.) immediately after each transfer was made. Data was analyzed using Microsoft Excel.

Results and Conclusions

Figure 5:
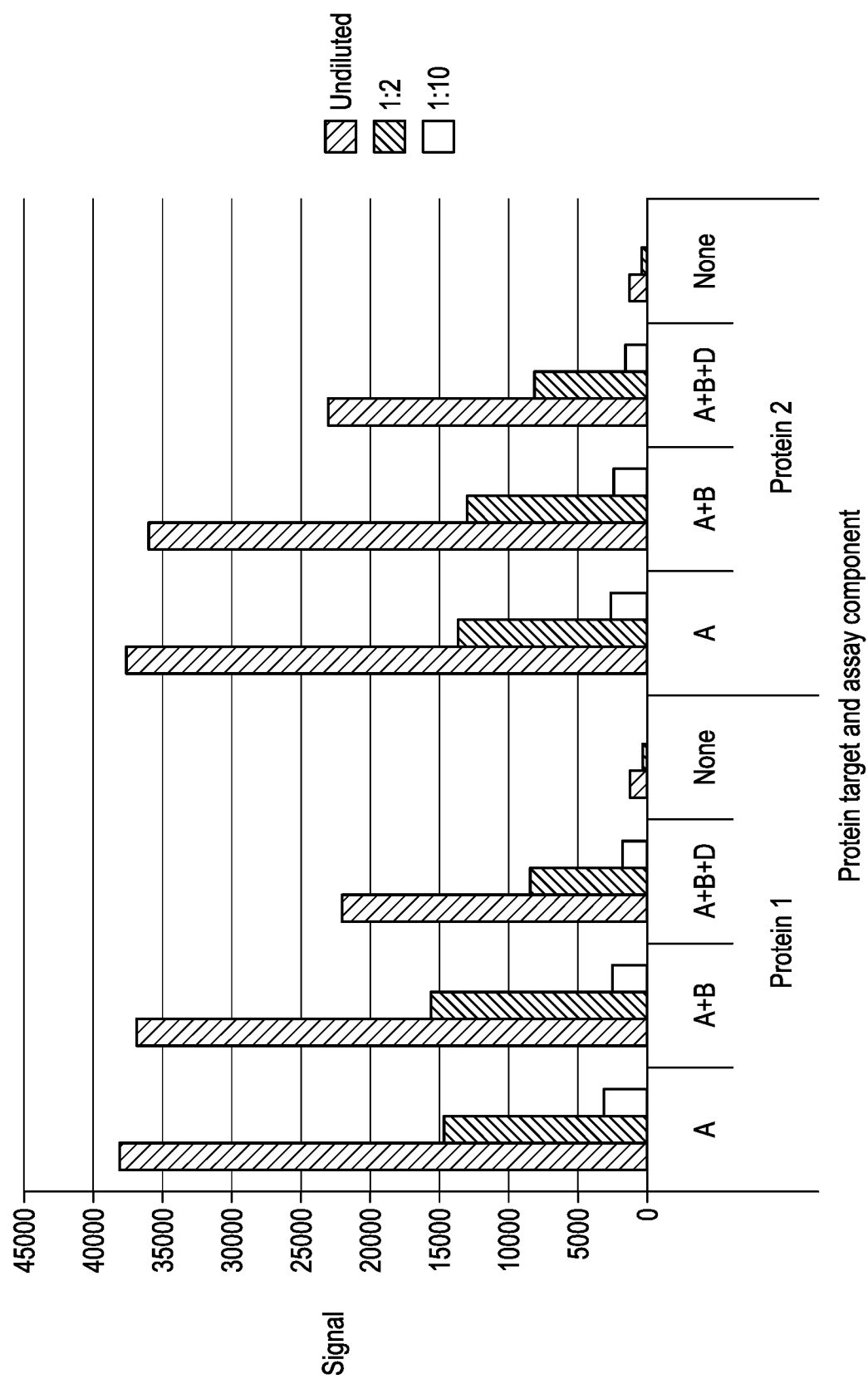
FIG. 5 shows background signal produced from wells containing known negative corn leaf extract and various combinations of assay components. Bars represent background signal produced after total incubation time of 120 minutes for undiluted, 1:2 and 1:10 negative extract titers. Assay chemistry used and chemistry components are displayed on the X-axis. "A" represents acceptor only, "A+B" represents acceptor bead and biotinylated antibody, "A+B+D" represents acceptor bead, biotinylated antibody and donor bead, "None" represents assay buffer only. Y-axis represents magnitude of background signal produced.

Results are summarized in FIG. 5. As observed in previous experiments, higher titers of negative leaf extract produced higher background signals for both assay chemistries used. Universally, conditions that combined extract and acceptor beads (conditions b and c above) produced the highest background signal. This result suggests that only acceptor and photosynthetic extract are required to produce background signal. This is consistent with the hypothesis that negative extract produces singlet oxygen, which causes emission from acceptor beads.

Compared to extract+acceptor conditions, addition of donor beads led to a reduction in signal. It is theorized this effect was caused by the blue dye or pigment in the donor beads. Blue dyes and/or pigments absorb both excitation and emission wavelengths (680 nm and 615 nm respectively), and may have led to the observed reduction in signal.

Example 3: Characterization of Photosynthetic and Non-Photosynthetic Negative Plant Extracts Methods Photosynthetic extracts have historically produced elevated background signals in the AlphaLISA® assay. To compare background signals from photosynthetic and non-photosynthetic tissues, negative extracts from corn leaf, soy leaf, corn root and soy root tissues were run in the AlphaLISA® assay. Negative corn leaf and soy leaf tissues were extracted as described in Example 1. Negative corn root tissue was extracted by adding 1-2 linear inches of root tissue to 24-well style PC vials (cat# PCVS 04-240-02, OPS Diagnostics, Lebanon N.J.). A ⅜" stainless steel ball bearing was added to each vial. 750 µl PBS extraction buffer, prepared as PBST extraction buffer with the omission of Tween-20, was added to each vial. Vials were macerated using a Geno/Grinder for 1 minute at 1650 rpm, then centrifuged at 3889×G for 10 minutes at 4 C to pellet debris. Root extract was removed from the vials and pooled. Total protein scores were collected using the Bradford assay, generally as described in Bradford (1976) (Bradford, M. M. (1976). A rapid and sensitive method for the quantitation of microgram quantities of protein utilizing the principle of protein-dye binding. Analytical biochemistry, 72(1), 248-254). A portion of each extracted tissue was used to prepare a duplicate sample extract set which was normalized to a total protein concentration of 0.2 mg/ml.

AlphaLISA® assay components were diluted to previously optimized concentrations using AlphaLISA® assay buffer. A total of two assay chemistries were prepared. Assay wells were prepared by adding 5 µl of each negative tissue extract (normalized and non-normalized) to a white half-area 96-well plate. 10 µl of biotinylated antibody solution was added to assay wells. 10 µl of antibody-conjugated acceptor bead solution was added to assay wells. 25 µl of donor bead solution was added to assay wells. Reaction plates were allowed to incubate at room temperature, protected from light, for approximately 2 hours before reading on an EnVision™ detector.

Results and Conclusions

Figure 6:
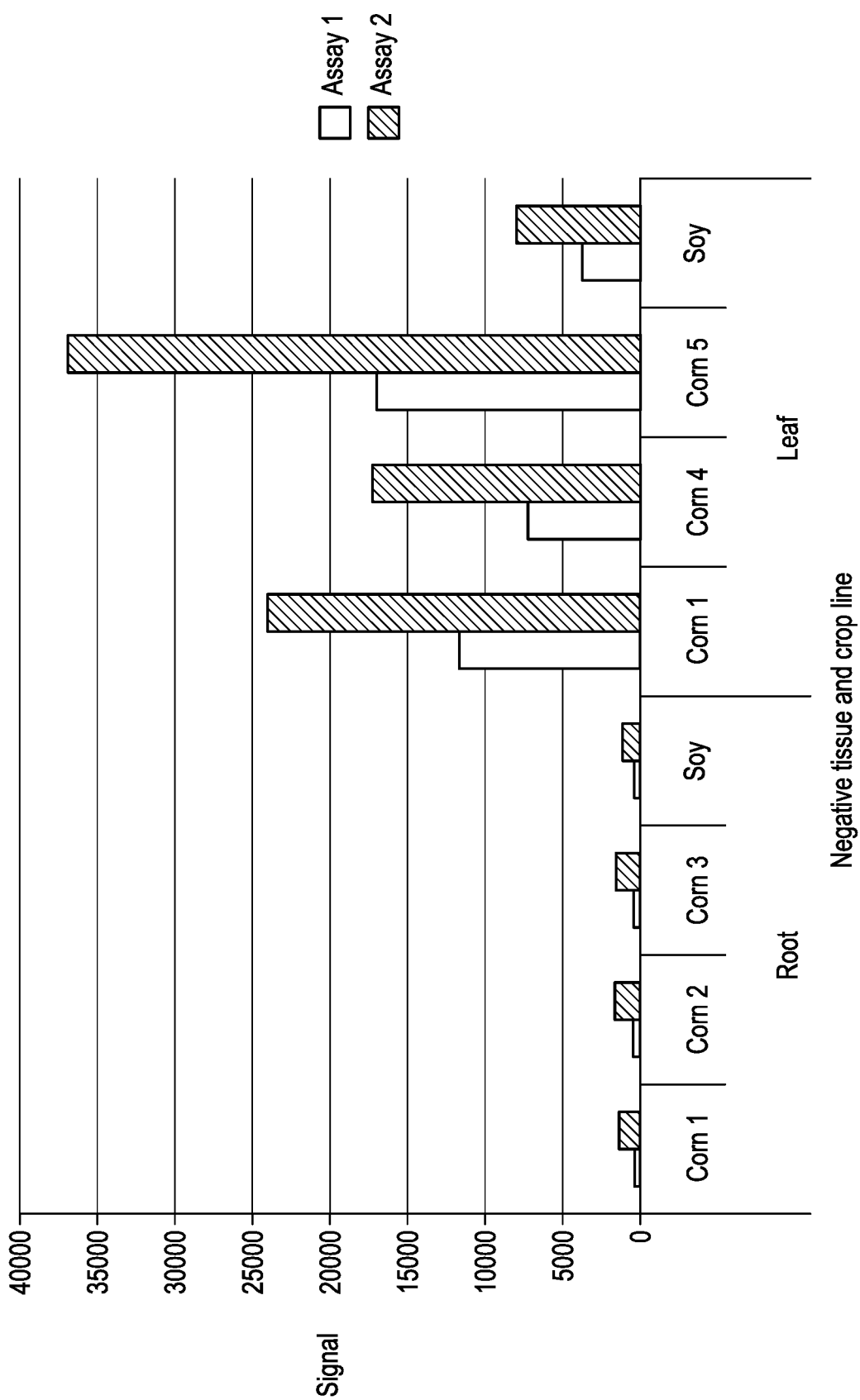
FIG. 6 shows background signal produced by corn and soy leaf and root tissue extract in two AlphaLISA® assays (commercially available from PerkinElmer). All tissue extracts were known to be negative for proteins of interest. Photosynthetic tissue extracts produce background signal which is significantly higher and more variable when compared to non-photosynthetic tissue extracts. Soy leaf extract produces significantly lower background signal when compared to corn leaf extracts.

Universally, non-photosynthetic tissue extract produced lower background signal when compared to photosynthetic tissue extract. Interestingly, background signal from soy leaf extract was significantly lower when compared to corn leaf extract. Total protein score did not show clear correlation with negative background signal. Signal obtained from negative extracts is summarized in FIG. 6.

When the photosystem is absent, as in root tissue, background signal is significantly reduced. This supports the hypothesis that background signal originates from some portion of the photosystem.

Example 4: Characterization of Chlorophyll's Influence on Background Signal

Methods

The photosystem has been linked with the production of background signal. Chlorophylls comprise a large portion of photosystem pigments, and are capable of absorbance at the AlphaLISA excitation wavelength of 680 nm. To evaluate chlorophyll's effect on background signal, purified chlorophyll and photosynthetic tissue extract were assayed using AlphaLISA. Negative leaf tissue was extracted as described in section 1. A powdered, water soluble chlorophyll (cat# C18300, Pfaltz & Bauer Inc., Waterbury Conn.) was dissolved in PBST extraction buffer to obtain a degree of color that is similar to what was observed in leaf extract.

AlphaLISA® assay components, including biotinylated antibody, antibody-conjugated acceptor beads and donor beads were diluted to previously-optimized concentrations using 1× AlphaLISA® assay buffer as diluent. 5 µl of chlorophyll solution, sample extract, or PBST extraction buffer was added to the wells of white half-area 96-well plates. Assay wells received AlphaLISA™ chemistry or 1× AlphaLISA® assay buffer. Wells which received AlphaLISA™ chemistry received 10 µl biotinylated antibody solution, 10 µl antibody-conjugated acceptor solution and 25 µl donor bead solution. Assay wells which received assay buffer only received 45 µl of 1× AlphaLISA® assay buffer. Plates were incubated at room temperature, protected from light, for approximately 2 hours after reagent addition. Following incubation, plates were read on an Envision. Data was analyzed using Microsoft Excel.

Results and Conclusions

Table 2 below shows the background signal produced by PBST extraction buffer, solubilized chlorophyll and negative leaf extract in the presence and absence of AlphaLISA® assay chemistry

| Average of Count Analyte | Chemistry Buffer | Protein 1 |
| --- | --- | --- |
| PBST | 65 | 305 |
| PBST and chlorophyll | 67 | 1821 |
| Maize leaf Neg | 597 | 10497 |
| Maize leaf Neg and chlorophyll | 498 | 8954 |

In the absence of AlphaLISA® assay chemistry components, background signal was very low. In the presence of AlphaLISA® assay chemistry, addition of chlorophyll significantly increased background signal. Highest background signal was obtained from sample extract.

Without wishing to be bound by any particular theory or mechanism, elevated background signal from wells containing only chlorophyll and assay chemistry suggest that samples which contain chlorophyll can lead to increased signal. Absorbance of light leads to the excitation of chlorophyll. Under normal photosynthetic conditions this excited molecule can pass electrons to an acceptor, however inefficient diffusion of this energy can lead to the production of triplet chlorophyll. This photosensitizer can react with triplet oxygen to produce singlet oxygen, the reactive agent which activates acceptor beads. Negative background signal could be significantly reduced by modifying AlphaLISA® donor bead chemistry to allow excitation at a wavelength of low photosystem absorbance (ex. 780 nm).

Example 5: Investigation of Photosystem Absorbance Spectra

Methods

To determine whether modifying donor beads for excitation at a wavelength of low photosystem absorbance significantly lowers background signal, spectral absorbance scans were performed using corn and soy leaf tissue extracts. Corn and soy leaf tissues were extracted as described in section 1. 200 µl of each tissue extract was loaded into the wells of a clear, flat-bottomed 96-well microtiter plate (cat# P7366 or equivalent, Sigma Aldrich, St. Louis Mo.). A spectral scan using wavelengths of 350-850 nm with an increment of 5 nm was performed using a Molecular Devices SpectraMAX absorbance reader (Molecular Devices, Sunnyvale Calif.).

Results and Conclusions

Figure 7:
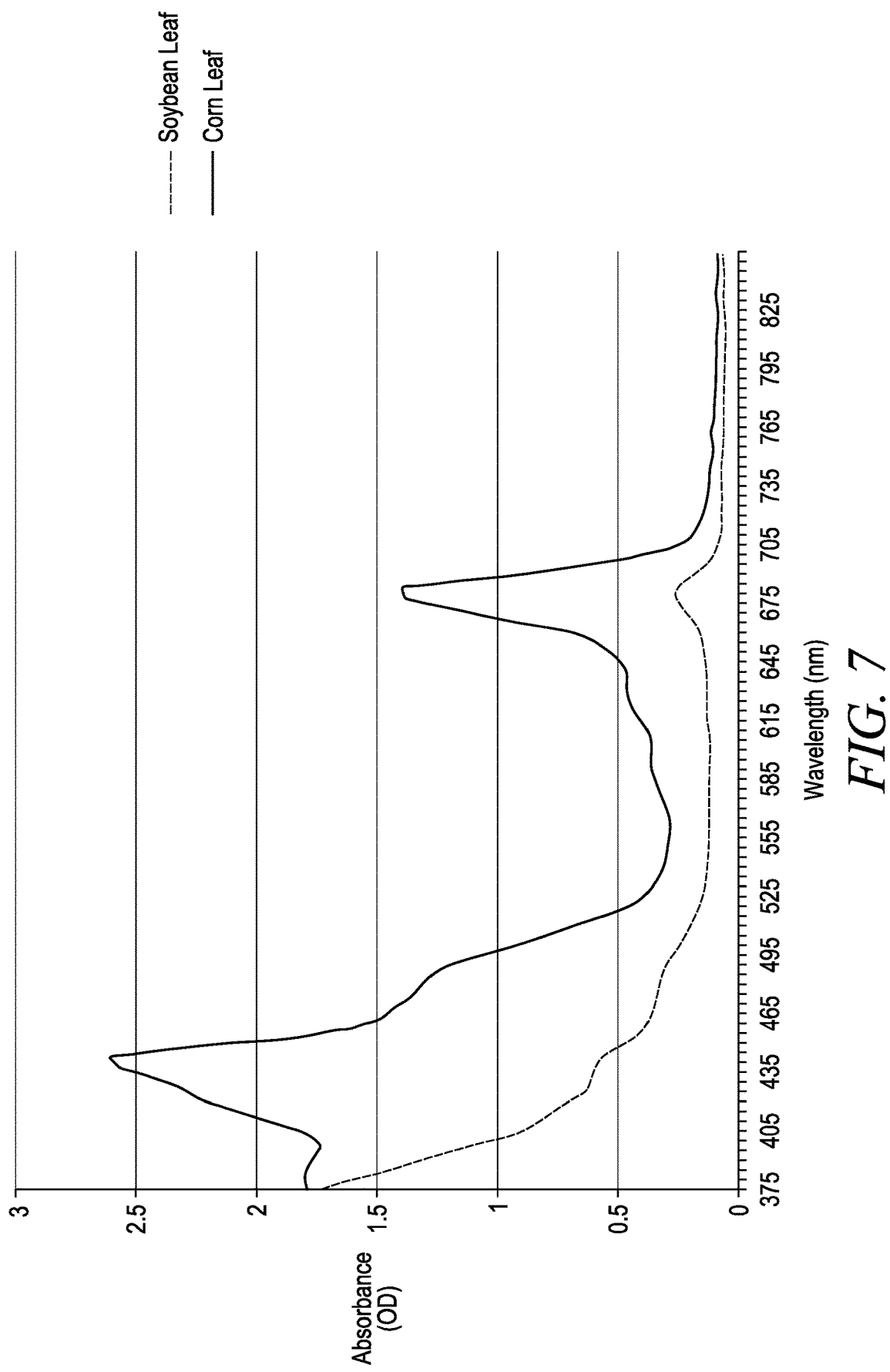
FIG. 7 shows a spectral absorbance scan of corn leaf and soybean leaf extracts. Absorbance wavelength is displayed on the X-axis. Absorbance density is displayed on the Y-axis. Corn and soybean leaf extracts show differences in 680 nm absorbance. Reduced 680 nm absorbance from soybean leaf extract coincides with its reduced background signal, as displayed in FIG. 6.

Chlorophyll produces a clear absorbance peak at 680 nm for photosynthetic tissues. High absorbance at 680 nm, the wavelength of donor bead excitation, may lead to production of triplet chlorophyll, which can convert ambient triplet oxygen to singlet oxygen. Lowest absorbance values were obtained at wavelengths above approximately 700 nm. Soy leaf tissue produced significantly lower absorbance at 680 nm when compared to corn leaf. This may explain why soy leaf tissue produced lower background signal in Example 3. Spectral scans for corn leaf and soy leaf extracts are presented in FIG. 7.

Example 6: Protein Extraction

Plant tissue from leaf, or other available organs, was sampled in 1.2 ml titertubes (Cat#84501XNBZQ, Quality Scientific Plastics, San Diego Calif.), and arranged in Deepwell Microplates (Cat# P9635FIS, Fisher Scientific, Pittsburgh Pa.). Two 3/16" ball bearings (Daisy Outdoor Products, Rogers Ark.) were added to each tube along with 500-700 µl PBST extraction buffer. PBST extraction buffer was prepared by addition of 0.05% Tween-20 detergent to a 1× reconstitution of Chloride-Phosphate Mixture (Cat# PW0002-30, EMD Millipore, Billerica Mass.). Tissue was ground at 1650 rpm for 1 minute in a Geno/Grinder 2010 (SPEX SamplePrep, Metuchen N.J.), then centrifuged for 10 minutes at 3889×G and 4° C. to pellet debris. Protein extract was removed from the pellet for processing, or assayed from the extraction plate.

Example 7: Assay Development—Sandwich Format—Hypothetical

Figure 8:
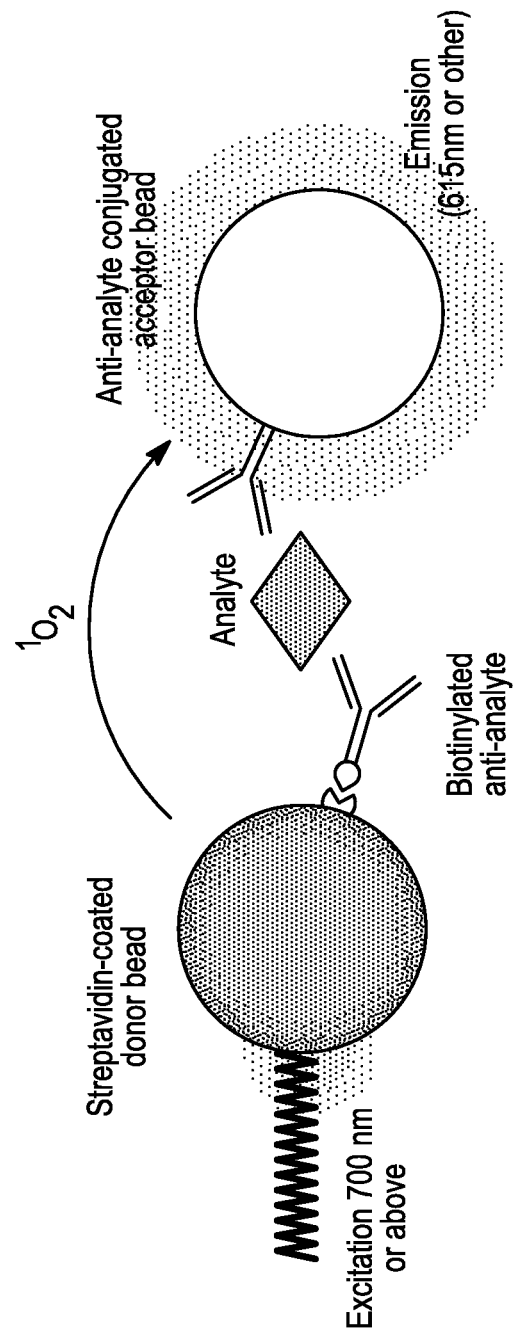
FIG. 8 is a cartoon showing one example of a sandwich assay format that reduces background signal when detecting one or more proteins of interest in a plant sample. The donor bead is excited by light having a wavelength outside the range of photosystem absorbance.

An Alpha assay is developed prior to use for protein screening. The goal of assay development is to create a condition whereby acceptor and donor beads are held in proximity due to affinity for the analyte, as outlined in FIG. 8. Assays are developed in sandwich format using streptavidin coated donor beads, biotinylated anti-analyte and acceptor beads conjugated with anti-analyte. Available antibodies are selected for antibody pair testing. Each antibody is biotinylated using ChromaLink Biotin antibody labeling kit per kit instructions (Solulink Inc, San Diego Calif.). Each antibody is conjugated to PerkinElmer AlphaLISA® acceptor beads as outlined in PerkinElmer's assay development guide.

Biotinylated antibodies, conjugated acceptor beads and streptavidin coated donor beads are prepared for pair testing by diluting in 1× AlphaLISA® assay buffer (Cat # AL000, PerkinElmer, Waltham Mass.). For each biotinylated antibody, a serial dilution series is prepared with concentrations ranging from 25 µg/ml to $1.5 \times 10^{-3}$ µg/ml in 4× increments. Each conjugated acceptor bead solution is diluted to 50 µg/ml. Donor bead is diluted to 80 µg/ml.

Pair testing reactions are prepared in half-area 96-well plates (Cat#6005560, PerkinElmer, Waltham Mass.). Analytes used include leaf tissue extracts from plants known to be positive and negative for the target protein, PBST buffer, and 100 µg/ml solution of purified target protein. Each analyte is screened against a matrix of antibody combinations, which includes all combinations of available conjugated acceptor beads and biotinylated serial dilution series. Reactions are prepared by adding 5 µl analyte, followed by 10 µl biotinylated antibody and 10 µl acceptor bead solution. Reactions are mixed using a microplate shaker and allowed to incubate at room temperature for approximately 1 hour. Following incubation, donor bead solution is added across all wells at 25 µl per well. Plates are allowed to incubate protected from light at room temperature for approximately 1 hour before quantifying signal using a BMG PHERAstar FS detector (BMG Labtech, Ortenberg Germany). Best pair is selected according to peak signal:noise ratio for positive:negative extract and purified protein:buffer.

After selecting an antibody pair and orientation, biotinylated antibody concentration is optimized. The biotinylated titer which produced highest positive signal during pairing is used as a median concentration. A serial titration is prepared ranging in concentration from 8× above to 8× below the median concentration with 2× increment. AlphaLISA® assay buffer is used as diluent. AlphaLISA reactions are prepared with the biotinylated titration as described above. Optimal biotinylated antibody titer is selected based on optimal signal:noise ratio. Optimal reagent concentrations are scaled to 20 µl total assay volume for compatibility with 384-well assay plates.

For quantitative applications, standard curve is developed by serial dilution of purified protein within a reasonable range. Optimal curve points and curve range are selected based on quadratic fit.

Example 8: Assay Development—Competitive Format—Hypothetical

Figure 9:
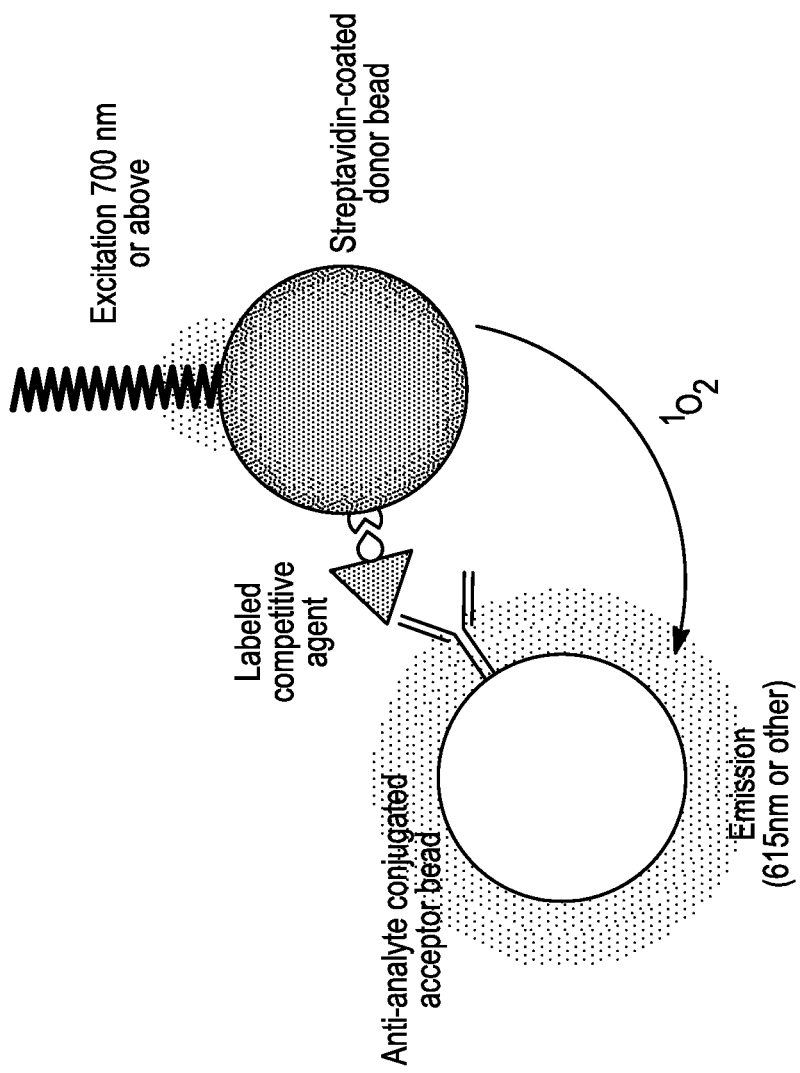
FIG. 9 is a cartoon showing one example of a competitive assay format that reduces background signal when detecting one or more proteins of interest in a plant sample. The donor bead is excited by light having a wavelength outside the range of photosystem absorbance.
Figure 10:
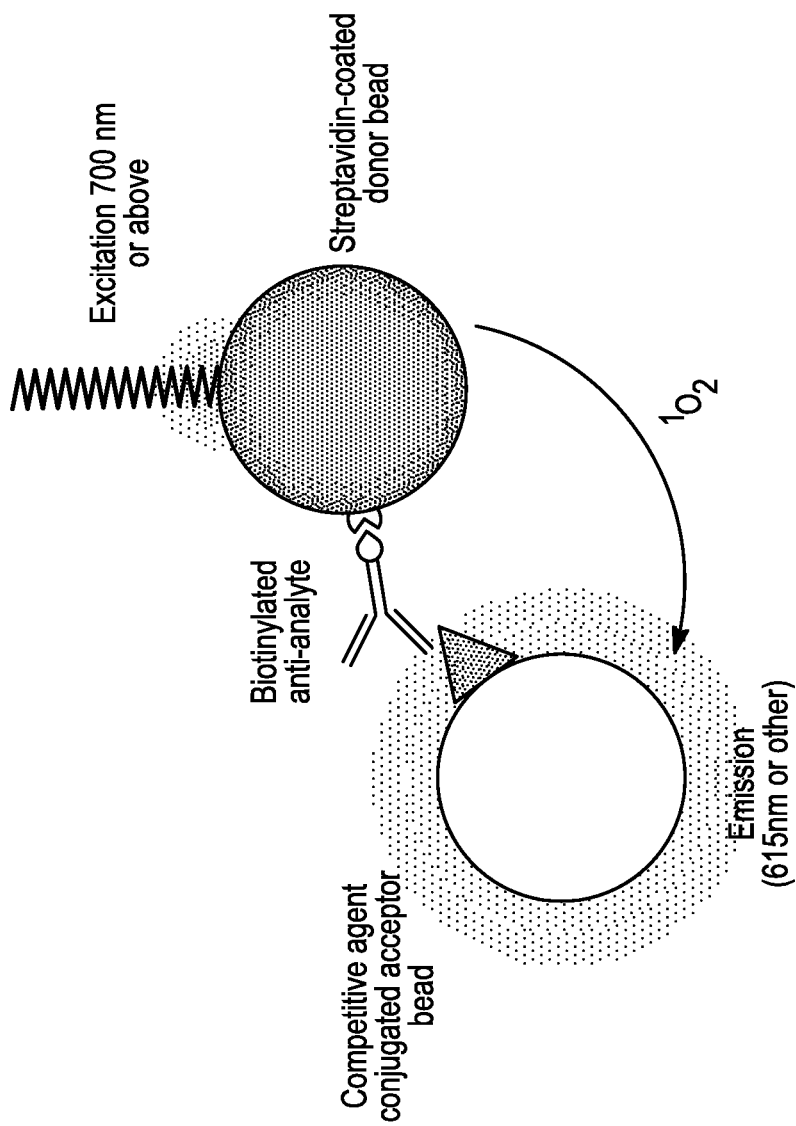
FIG. 10 is a cartoon showing another example of another competitive assay format that reduces background signal when detecting one or more proteins of interest in a plant sample. The donor bead is excited by light having a wavelength outside the range of photosystem absorbance.

As opposed to sandwich assays, competitive assays are developed to produce signal in the absence of target protein, as outlined in FIGS. 9 and 10. Presence of the target protein eliminates proximity between acceptor and donor beads, leading to reduced signal. Competitive assays are developed in competitive format using acceptor beads, donor beads, an anti-analyte ligand and a competitive agent. Streptavidin coated donor beads and aldehyde-bearing conjugation-ready acceptor beads and are available from PerkinElmer. The ligand and competitive agent should each be designed to associate with a separate bead species by conjugation or affinity. The competitive agent can be directly conjugated to the acceptor bead and paired with a biotinylated antibody. Conversely, the antibody can be directly conjugated to the acceptor bead and paired with a biotinylated competitive agent.

Available antibodies are selected for antibody pair testing. Each antibody is biotinylated using ChromaLink Biotin antibody labeling kit per instructions (Solulink Inc, San Diego Calif.). Each antibody is also conjugated to PerkinElmer AlphaLISA acceptor beads as outlined in PerkinElmer's assay development guide.

A competitive agent is designed and synthesized using protein expression and purification techniques. The competitive agent should mimic the target protein's properties of affinity. The competitive agent is biotinylated using ChromaLink Biotin labeling kit or equivalent. The competitive agent is also conjugated to PerkinElmer AlphaLISA acceptor beads. There are many methods for conjugation of the competitive agent. Optimal method will depend upon the properties of the competitive agent. Competitive agent bead conjugation may utilize reductive amination as used for antibody conjugation. Alternatively, the acceptor's aldehyde groups may be modified using maleimide or haloacetyles to allow for sulfhydryl coupling. The bead's aldehyde groups may also be oxidized to carboxyl groups to allow for EDC reaction chemistry crosslinking.

Reagents are separated into groups for two assay orientations: labeled competitive agent, and conjugated competitive agent. Labeled competitive agent assay chemistry contains acceptor beads which have been previously conjugated to various antibodies, streptavidin coated donor beads, and biotinylated competitive agent. Conjugated competitive agent assay chemistry contains acceptor beads which have been previously conjugated with competitive agent, streptavidin coated donor beads, and various biotinylated antibodies.

Reagents are prepared for antibody and orientation selection by diluting in 1× AlphaLISA® assay buffer (Cat # AL000, PerkinElmer, Waltham Mass.). For labeled competitive agent orientation, the competitive agent is diluted serially to prepare concentrations ranging from 25 µg/ml to $1.5 \times 10^{-3}$ µg/ml in 4× increments. For conjugated competitive agent orientation, each biotinylated antibody is diluted serially to prepare concentrations ranging from 25 µg/ml to $1.5 \times 10^{-3}$ µg/ml in 4× increments. For both orientations, acceptor beads are diluted to 50 µg/ml and donor beads are diluted to 80 µg/ml.

Antibody and orientation selection reactions are prepared in half-area 96-well plates (Cat#6005560, PerkinElmer, Waltham Mass.). Analytes used include leaf tissue extracts from plants known to be positive and negative for the target protein, PBST buffer, and 100 µg/ml solution of purified target protein. Each analyte is screened against a matrix of assay orientations and antibody concentrations, which includes all combinations of available conjugated acceptor beads, biotinylated antibodies and biotinylated competitive reagent. Labeled competitive agent orientation reactions are prepared by adding 5 µl analyte followed by 10 µl antibody-conjugated acceptor bead solution and 10 µl competitive agent solution. Reactions are mixed using a microplate shaker and allowed to incubate at room temperature for approximately 1 hour. Following incubation, donor bead solution is added across all wells at 25 µl per well. For conjugated competitive agent orientation, reactions are prepared by adding 5 µl analyte followed by 10 µl competitive agent-conjugated acceptor bead solution and 10 µl biotinylated antibody solution. Reactions are mixed using a microplate shaker and allowed to incubate at room temperature for approximately 1 hour. Following incubation, donor bead solution is added across all wells at 25 µl per well. After addition of donor, plates are allowed to incubate protected from light at room temperature for approximately 1 hour before quantifying signal using a BMG PHERAstar FS detector (BMG Labtech, Ortenberg Germany). Best antibody and orientation is selected according to peak signal:noise ratio for positive:negative extract and purified protein:buffer.

After selecting an antibody and orientation, concentration of biotinylated antibody or biotinylated competitive agent is optimized. The procedure for this optimization differs depending upon the orientation that has been selected.

If antibody and orientation testing reveals that labeled competitive agent orientation is optimal, a serial titration is prepared for the biotinylated competitive agent. Concentrations used range from 8× above to 8× below the median concentration of which produced best separation between positive and negative signals during the antibody and orientation selection experiment. AlphaLISA® assay buffer is used as diluent. Analytes used include leaf tissue extracts from plants known to be positive and negative for the target protein, PBST buffer, and 100 µg/ml solution of purified target protein. AlphaLISA reactions are prepared by adding 5 µl analyte followed by 10 µl antibody-conjugated acceptor bead solution and 10 µl competitive agent solution for each concentration of the serial dilution series. Reactions are mixed using a microplate shaker and allowed to incubate at room temperature for approximately 1 hour. Following incubation, donor bead solution is added across all wells at 25 µl per well. After addition of donor, plates are allowed to incubate protected from light at room temperature for approximately 1 hour before quantifying signal using a BMG PHERAstar FS detector (BMG Labtech, Ortenberg Germany). Optimal competitive agent concentration is selected according to peak signal:noise ratio for positive:negative extract and purified protein:buffer. Optimal reagent concentrations are scaled to 20 µl total assay volume for compatibility with 384-well assay plates.

If antibody and orientation testing reveals that conjugated competitive agent orientation is optimal, a serial titration is prepared for the biotinylated antibody. Concentrations used range from 8× above to 8× below the median concentration of which produced best separation between positive and negative signals during the antibody and orientation selection experiment. AlphaLISA® assay buffer is used as diluent. Analytes used include leaf tissue extracts from plants known to be positive and negative for the target protein, PBST buffer, and 100 µg/ml solution of purified target protein. AlphaLISA reactions are prepared by adding 5 µl analyte followed by 10 µl competitive agent-conjugated acceptor bead solution and 10 µl biotinylated antibody solution for each concentration of the serial dilution series. Reactions are mixed using a microplate shaker and allowed to incubate at room temperature for approximately 1 hour. Following incubation, donor bead solution is added across all wells at 25 µl per well. After addition of donor, plates are allowed to incubate protected from light at room temperature for approximately 1 hour before quantifying signal using a BMG PHERAstar FS detector (BMG Labtech, Ortenberg Germany). Optimal biotinylated antibody concentration is selected according to peak signal:noise ratio for positive:negative extract and purified protein:buffer. Optimal reagent concentrations are scaled to 20 µl total assay volume for compatibility with 384-well assay plates.

For quantitative applications, standard curve is developed by serial dilution of purified protein within a reasonable range. Optimal curve points and curve range are selected based on quadratic fit.

Example 9: Assay Preparation—Hypothetical

5 µl analyte is added to a white 384-well proxiplate (Cat#6006290, PerkinElmer, Waltham Mass.) using a Dynamic Devices Lynx liquid handler (Dynamic Devices, Wilmington Del.). Analyte includes sample extract and standard curve for applicable applications. 5 µl of a mixture containing appropriately-titered biotinylated antibody and antibody-conjugated acceptor bead is added to the assay wells. The reaction plate is allowed to incubate for approximately 1 hour at room temperature to allow binding. After incubation, 10 µl appropriately-titered streptavidin-coated donor beads are added to the assay wells. The reaction plate is allowed to incubate at room temperature for approximately 1 hour to allow streptavidin-coated donor beads to bind to available biotinylated antibody in solution. After all reagent additions and incubations are complete, signal is quantified in an appropriately-configured PHERAstar FS microplate reader.

Example 10: Signal Quantification—Hypothetical

Figure 12:
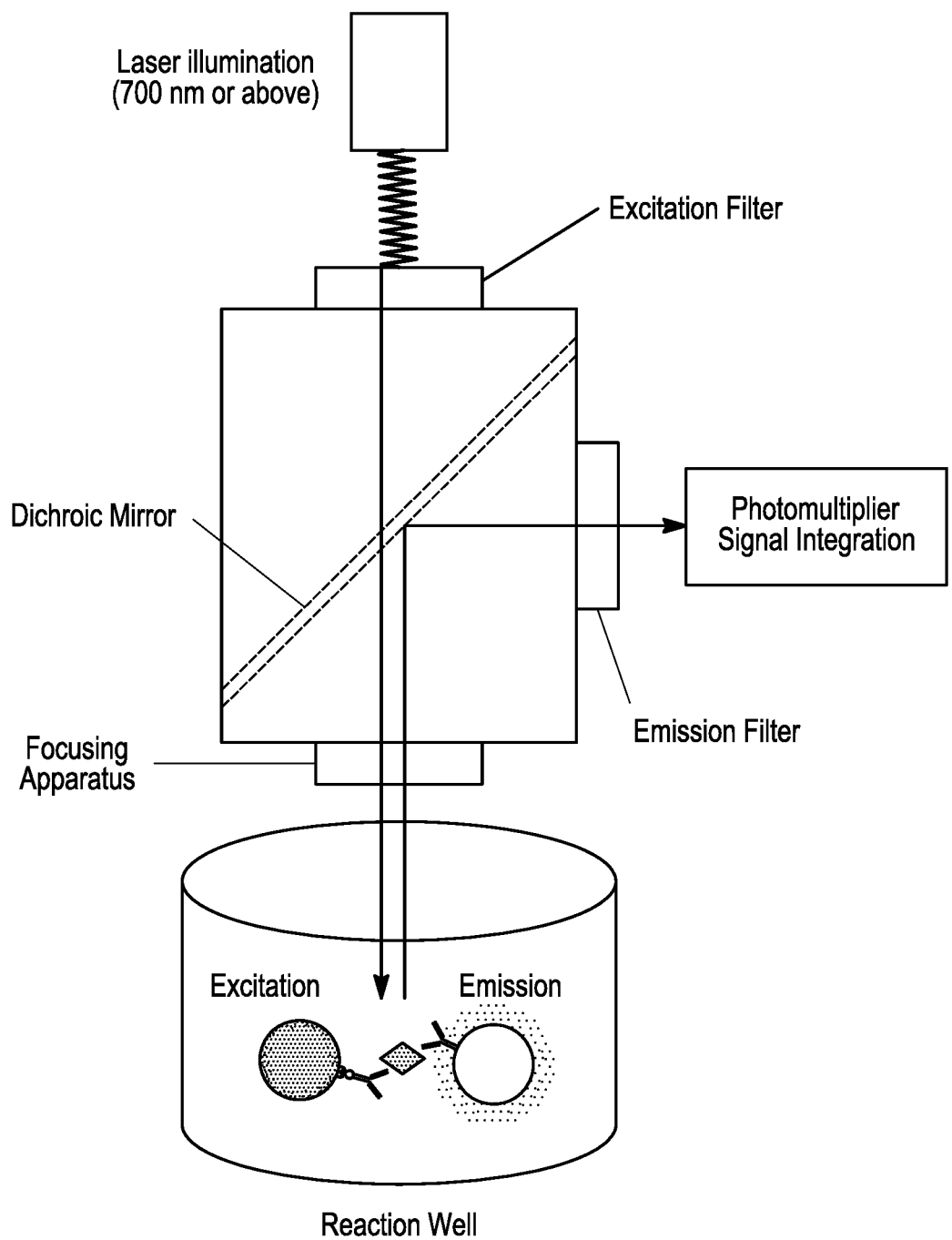
FIG. 12 shows one example of a Configuration of Detection Optics Module. Laser diode supplies light for donor bead excitation. Light produced by laser passes through an excitation filter to condition light and remove stray wavelengths. Filtered laser light passes through a dichroic mirror and illuminates the reaction well, causing excitation of modified donor bead. Proximal transfer of singlet oxygen leads to emission of signal from acceptor bead. Emission signal is recaptured by optic module, reflecting off of the dichroic mirror and passing through an emission filter to condition light and remove non-integrated wavelengths. Filtered emission light is integrated using a photomultiplier. Wavelengths for excitation filter, dichroic mirror and emission filter should be appropriately tuned to the application.

A chemiluminescence and/or fluorescence reader, such as PHERAstar FS unit, is retrofitted with an appropriate laser for donor bead excitation at 780 nm or other wavelength (example cat# PH780DBR040BF, Photodigm Inc, Richardson Tex.). A light filter is installed to condition excitation to 780 nm+/−5 nm. A dichroic mirror is installed to allow passage of light above 700 nm, and reflection of light below 700 nm. An emission filter is installed to allow conditioning of emission light to 615 nm+/−8 nm. Wells are excited for a length of time sufficient for donor bead excitation. Following a delay that reduces interference from stray signal, the emission signal is captured and integrated for a time sufficient for signal quantification. The focal height is set so an appropriate amount of light reaches the detector. Emission signal is quantitated by photomultiplier with gain set to a value that allows for appropriate quantification of signal. One example of optics module is outlined in FIG. 12.

We claim:

1. A method of detecting one or more proteins of interest in a plant sample, the method comprising:
   a. incubating the plant sample comprising the one or more proteins of interest with a donor bead associated with a donor-associated analyte detection reagent and an acceptor bead associated with an acceptor-associated analyte detection reagent, wherein the plant sample is from a photosynthetic tissue, and wherein the donor-associated analyte detection reagent and the acceptor-associated analyte detection reagent are capable of interacting with the one or more proteins of interest;
   b. exciting the donor bead with light having a wavelength outside the range of photosystem absorbance for the plant sample, wherein the donor bead is not excited with light having a wavelength of 680 nm;
   c. capturing the emission of light; and
   d. determining the presence or absence of the one or more proteins of interest of in the plant sample based on the emission, whereby signal intensity indicates presence, absence, or concentration of the one or more proteins of interest within the plant sample.

2. The method of claim 1, further comprising quantifying the emission of light.

3. The method of claim 1, the method further comprising: capturing the emission at a wavelength that is lower than the excitation wavelength.

4. The method of claim 1, wherein the donor bead comprises single or multiple photoactive substances that allow the donor bead to be excited at one or more wavelengths.

5. The method of claim 1, wherein the donor bead comprises a photoactive substance that absorbs primarily at about 780 nm.

6. The method of claim 1, wherein the singlet oxygen production is reduced as compared to a control wherein the control donor bead is excited with light having a wavelength of about 680 nm.

7. The method of claim 1, wherein the method is high throughput.

8. The method of claim 1, wherein the plant sample is a photosynthetic tissue extract.

9. The method of claim 1, wherein the plant sample is a protein extract.

10. The method of claim 1, wherein the method decreases background signal caused by the production of singlet oxygen by excitation of photosystem pigments in the plant sample.

11. The method of claim 10, wherein the method decreases chemiluminescence background signal by 5%, 10%, 15%, 20%, 25%, 30%, 35%, 40%, 45%, 50%, 55%, 60%, 65%, 70%, 75%, 80%, 85%, 90%, 95%, or 100% as compared to a control wherein the control donor bead is excited with light having a wavelength of 680 nm.

12. The method of claim 1, wherein the donor bead is excited with light having a wavelength from about 200 nm to 670 nm.

13. The method of claim 1, wherein the donor bead is excited with light having a wavelength from about 690 nm to 1100 nm.

14. The method of claim 1, wherein the donor-associated analyte detection reagent is conjugated or preconjugated to the donor bead.

15. The method of claim 1, wherein the acceptor-associated analyte detection reagent is conjugated or preconjugated to the acceptor bead.

16. The method of claim 1, wherein the donor-associated analyte detection reagent and/or acceptor-associated analyte detection reagent is conjugated to a secondary reagent.

17. The method of claim 1, wherein the acceptor or donor bead is conjugated to a secondary reagent.

18. The method of claim 17, wherein the secondary reagent comprises ligands, receptors, antibodies, antigens, lipids, carbohydrates, peptides, oligosaccharides, lectins, nucleic acids, aptamers, epitope tags, a metal, biotin, avidin, streptavidin, or digoxigenin.

19. The method of claim 1 wherein the one or more proteins of interest confers a trait.

20. The method of claim 19, wherein the one or more proteins of interest confers a trait for agronomics, insect resistance, disease resistance, herbicide resistance, sterility, grain characteristics, nutrient, metabolism, digestibility, kernel size, or sucrose loading.

21. The method of claim 1, wherein the method comprises one or more acceptor-associated analyte detection reagents that binds to or interacts with one, two or more different proteins of interest.

22. The method of claim 1, wherein the method comprises one or more donor associated analyte detection reagents that binds to or interacts with one, two or more proteins of interest.

23. The method of claim 1, wherein the method comprises one or more different types of acceptor beads that have different emission wavelengths.

24. The method of claim 1, wherein the method comprises one or more different types of donor beads that have different excitation wavelengths.

\* \* \* \* \*